US012590088B2

(12) United States Patent
Kang et al.

(10) Patent No.: US 12,590,088 B2
(45) Date of Patent: Mar. 31, 2026

(54) JAK INHIBITOR COMPOUND AND PHARMACEUTICAL COMPOSITION INCLUDING THE SAME

(71) Applicant: KOREA PHARMA CO., LTD., Hwaseong-si (KR)

(72) Inventors: Soosung Kang, Incheon (KR); Eun Sun Park, Gwangyang-si (KR); Eun Hee Park, Seoul (KR); Seung Hee Han, Suwon-si (KR)

(73) Assignee: KOREA PHARMA CO., LTD., Hwaseong-si (KR)

(*) Notice: Subject to any disclaimer, the term of this patent is extended or adjusted under 35 U.S.C. 154(b) by 980 days.

(21) Appl. No.: 17/613,291

(22) PCT Filed: May 27, 2020

(86) PCT No.: PCT/KR2020/006872
§ 371 (c)(1),
(2) Date: Nov. 22, 2021

(87) PCT Pub. No.: WO2020/242204
PCT Pub. Date: Dec. 3, 2020

(65) Prior Publication Data

US 2022/0220109 A1 Jul. 14, 2022

(30) Foreign Application Priority Data

May 27, 2019 (KR) ........................ 10-2019-0061923

(51) Int. Cl.
*C07D 471/04* (2006.01)

(52) U.S. Cl.
CPC .................................. *C07D 471/04* (2013.01)

(58) Field of Classification Search
CPC .. C07D 471/04; A61K 31/437; A61K 31/439; A61K 31/4545; A61K 31/46; A61K 31/55; A61P 35/00; A61P 37/00
See application file for complete search history.

(56) References Cited

U.S. PATENT DOCUMENTS

2007/0135461 A1 6/2007 Rodgers et al.
2010/0105661 A1* 4/2010 Shirakami ............... A61P 29/00
514/252.04
2014/0011795 A1 1/2014 Wrobleski et al.
2016/0176850 A1 6/2016 Johnson et al.
2018/0310340 A1 10/2018 Noh et al.

FOREIGN PATENT DOCUMENTS

KR 10-2008-0081194 A 9/2008
KR 10-2009-0106604 A 10/2009
WO WO-2007007919 A2 * 1/2007 ......... A61K 31/4745
WO WO-2007077949 A1 * 7/2007 ........... A61K 31/437
WO WO-2019107943 A1 * 6/2019 ........... A61K 31/437

OTHER PUBLICATIONS

Purandare et al., Leukemia, 26, 280-288 (2012).
Schwartz et al., Nat. Rev. Rheumatol., 12(1): 25-36 (2016).
Thoma et al., Bioorganic & Medicinal Chemistry Letters, 24, 4617-4621 (2014).
Vainchenker et al., F1000Research 2018, 7(F1000 Faculty Rev): 82, Jan. 17, 2018.

* cited by examiner

*Primary Examiner* — Joseph K McKane
*Assistant Examiner* — Ashli Ariana Chicks
(74) *Attorney, Agent, or Firm* — Lee IP Law, P.C.

(57) ABSTRACT

The present invention relates to a JAK inhibitor compound and a pharmaceutical composition including the same. More specifically, the present invention relates to a compound of Formula I or a pharmaceutically acceptable salt thereof and a pharmaceutical composition including the same. The structure of the compound of Formula I is described in the specification. The compound of the present invention can exhibit therapeutic effects on a variety of diseases, for example, inflammatory diseases, autoimmune diseases, myeloproliferative diseases, and human cancers due to its ability to regulate signal transduction at the level of JAK kinases.

4 Claims, No Drawings

JAK INHIBITOR COMPOUND AND PHARMACEUTICAL COMPOSITION INCLUDING THE SAME

CROSS REFERENCE TO RELATED APPLICATIONS

This is the U.S. national phase application based on PCT Application No. PCT/KR2020/006872, filed May 27, 2020, which is based on Korean Patent Application No. 10-2019-0061923, filed May 27, 2019, the entire contents of all of which are hereby incorporated by reference.

TECHNICAL FIELD

The present invention relates to a JAK inhibitor compound and a pharmaceutical composition including the same.

BACKGROUND ART

Protein kinases (PKs) are a group of enzymes that regulate diverse, important biological processes, including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases, including cancer. A subset of protein kinases (also referred to as oncogenic protein kinases), when dysregulated, can cause tumor formation and growth, and further contribute to tumor maintenance and progression. Thus far, oncogenic protein kinases represent one of the largest and most attractive groups of protein targets for cancer intervention and drug development.

The Janus kinase (JAK) family plays a critical role in the cytokine-dependent regulation of proliferation and function of cells involved in immune response. At present, there are four known mammalian JAK family members: JAK1 (Janus kinase-1), JAK-2 (Janus kinase-2), JAK3 (Janus kinase-3) and TYK2 (protein-tyrosine kinase 2). The JAK proteins have a size ranging from 120 kDa to 140 kDa and comprise 7 conserved JAK homology (JH) domains. One of them is a functional catalytic kinase domain, and another is a pseudokinase domain which potentially exerts a regulatory function and/or acts as a docking site for STATs.

JAK1 is involved in most signal transduction pathways mediated by cytokines such as γc cytokines (IL-2, IL-4, IL-7, IL-9, IL-21), members of the gp130 cytokine family (IL-6, IL-11, LIF, OSM), members of the IRF family, and IL-10-like cytokines and regulates the functions of T-cells and B-cells (Non-Patent Document 1). Thus, JAK1 is being developed for the treatment of diseases such as rheumatoid arthritis, inflammatory bowel disease, atopic dermatitis, and psoriasis.

JAK2 is used for signal transduction in which cytokines such as pc cytokines, gp130 cytokine family members, EPO, IRF, IL-12, and IL-23 are involved. Particularly, when cytokines such as EPO, TPO, IL-3, and IL-5 bind to their receptors, JAK2 kinases tend to homodimerize and are ultimately involved in myeloid differentiation and haematopoiesis as well as T cell proliferation. Thus, selective JAK2 inhibitors are being developed for the treatment of myeloproliferative disorders such as myeloproliferative neoplasms (Non-Patent Document 2).

The expression of JAK3 is more restricted than that of other JAK kinases. When γc cytokines bind to their receptors, JAK3 is involved only in a single pathway through dimerization with JAK1. Thus, JAK3 inhibitors can be used to treat diseases such as rheumatoid arthritis and psoriasis (Non-Patent Document 3). JAK3 selective inhibitors are likely to cause fewer side effects than other inhibitors, but their efficacy may also be low compared to other inhibitors because they are involved only in a single pathway among various immune-related JAK/STAT pathways (Non-Patent Document 4).

Furthermore, blocking signal transduction at the level of JAK kinases also hold promise for developing treatments for various diseases, for example, inflammatory diseases, autoimmune diseases, myeloproliferative diseases, and human cancers and may result in therapeutic benefits in patients suffering from immune disorders of the skin such as psoriasis and skin sensitization.

Accordingly, inhibitors of Janus kinases or related kinases are widely sought and several patent publications report effective classes of compounds. For example, certain JAK inhibitors, including pyrrolopyridine and pyrrolopyrimidine compounds, are disclosed in U.S. Patent Publication No. 2007/0135461 A1 (Patent Document 1).

The entire disclosure of all prior art documents cited above is incorporated herein by reference.

(Patent Document 1) US 2007/0135461 A1 (Jun. 14, 2007)

(Non-Patent Document 1) SCHWARTZ, Daniella M., et al. Type I/II cytokines, JAKs, and new strategies for treating autoimmune diseases. *Nature Reviews Rheumatology,* 2016, 12.1: 25.

(Non-Patent Document 2) PURANDARE, A. V., et al. Characterization of BMS-911543, a functionally selective small-molecule inhibitor of JAK2. *Leukemia,* 2012, 26.2: 280.

(Non-Patent Document 3) VAINCHENKER, William, et al. JAK inhibitors for the treatment of myeloproliferative neoplasms and other disorders. F1000Research, 2018, 7.

(Non-Patent Document 4) THOMA, Gebhard; DRUECKES, Peter; ZERWES, Hans-Guenter. Selective inhibitors of the Janus kinase Jak3—Are they effective?, *Bioorganic & medicinal chemistry letters,* 2014, 24.19: 4617-4621.

DETAILED DESCRIPTION OF THE INVENTION

Problems to be Solved by the Invention

As described above, JAK kinases such as JAK1, JAK2, and JAK3 have their own characteristics. The present inventors have intended to develop a drug that selectively inhibits JAK1 so as to be more effective against most inflammation and autoimmune related diseases for better efficacy.

However, it is difficult to enhance the activities of ATP-binding kinase domains of all JAK family members for specific kinases because the structural differences of the kinase domains are not very significant.

The present inventors have referred to previously developed inhibitors whose structures are known to choose an initial structure, and as a result, succeeded in finding an inhibitor that not only exhibits high affinity for JAK1, but also acts more selectively on JAK than on other JAK kinases. The present invention has been accomplished based on this finding. An object of the present invention is to provide a novel compound that has high inhibitory activity against Janus kinases, particularly JAK1.

Means for Solving the Problems

The present invention has been made in an effort to solve the problems of the prior art and provides a compound represented by Formula I:

[Formula I]

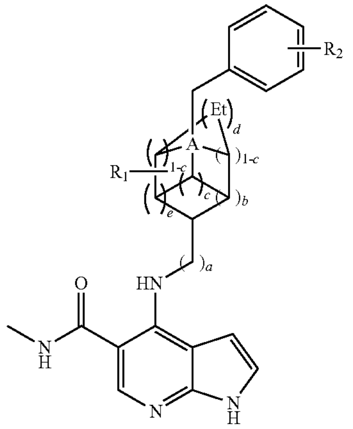

wherein $R_1$ is hydrogen, $C_1$-$C_3$ alkyl or halogen, $R_2$ is hydrogen, halogen, cyan or $C_1$-$C_3$ alkoxy, a and b are each independently an integer from 0 to 2, c and d are each independently an integer of 0 or 1 and satisfy the relationship c+d≤1, e is an integer of 1 or 2 and satisfies the relationship e≤3−b, A is a secondary or tertiary amine structurally capable of forming chemical bonds, and Et is ethyl, provided that when c or d is 1, b and e are all 1 (b=e=1), or a pharmaceutically acceptable salt thereof.

In Formula I, b and e are all 1, c is 0, d is 1, $R_1$ is hydrogen, and $R_2$ is chlorine.

In Formula I, b and e are all 1, e is 0, d is 0, $R_1$ is methyl or fluorine, and $R_2$ is chlorine or methoxy.

The compound represented by Formula I or pharmaceutically acceptable salt thereof is a compound represented by Formula II:

[Formula II]

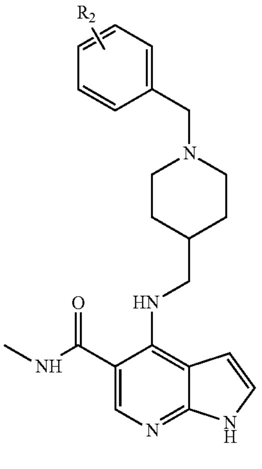

wherein $R_2$ is hydrogen, halogen, cyan or $C_1$-$C_3$ alkoxy, or a pharmaceutically acceptable salt thereof.

The compound represented by Formula I or pharmaceutically acceptable salt thereof is a compound represented by Formula III:

[Formula III]

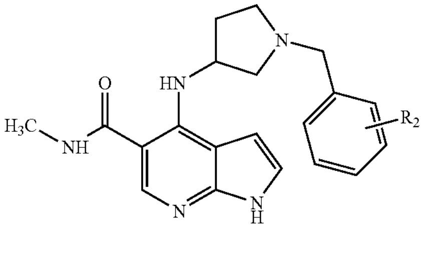

wherein $R_2$ is hydrogen, halogen, cyan or $C_1$-$C_3$ alkoxy, or a pharmaceutically acceptable salt thereof.

The compound represented by Formula I or pharmaceutically acceptable salt thereof is a compound represented by Formula IV:

[Formula IV]

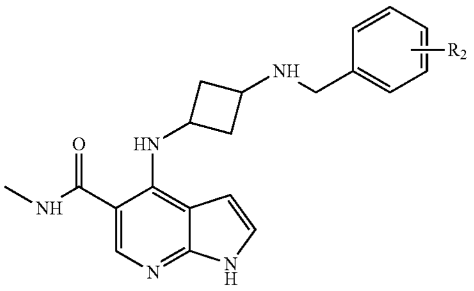

wherein $R_2$ is hydrogen, halogen, cyan or $C_1$-$C_3$ alkoxy, or a pharmaceutically acceptable salt thereof.

The compound represented by Formula I or pharmaceutically acceptable salt thereof is a compound represented by Formula V:

[Formula V]

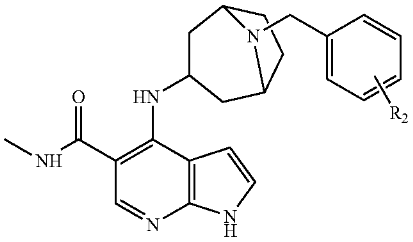

wherein $R_2$ is hydrogen, halogen, cyan or $C_1$-$C_3$ alkoxy, or a pharmaceutically acceptable salt thereof.

The compound represented by Formula I or pharmaceutically acceptable salt thereof is a compound represented by Formula VI:

[Formula VI]

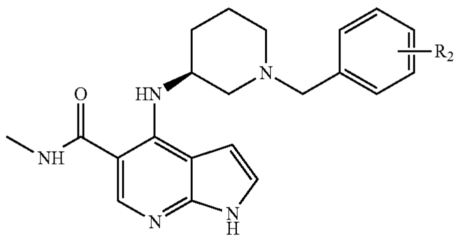

wherein $R_2$ is hydrogen, halogen, cyan or $C_1$-$C_3$ alkoxy, or a pharmaceutically acceptable salt thereof.

The compound represented by Formula I or pharmaceutically acceptable salt thereof is a compound represented by Formula VII:

[Formula VII]

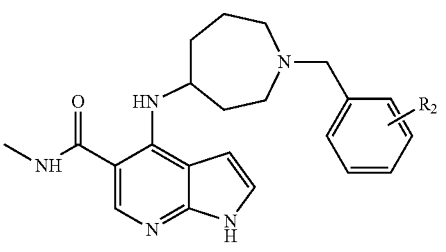

wherein $R_2$ is hydrogen, halogen, cyan or $C_1$-$C_3$ alkoxy, or a pharmaceutically acceptable salt thereof.

The compound represented by Formula I or pharmaceutically acceptable salt thereof is a compound represented by Formula VIII:

[Formula VIII]

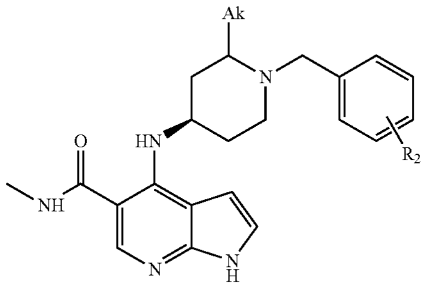

wherein Ak is $C_1$-$C_3$ alkyl and $R_2$ is hydrogen, halogen, cyan or $C_1$-$C_3$ alkoxy, or a pharmaceutically acceptable salt thereof.

The compound represented by Formula I or pharmaceutically acceptable salt thereof is a compound represented by Formula IX:

[Formula IX]

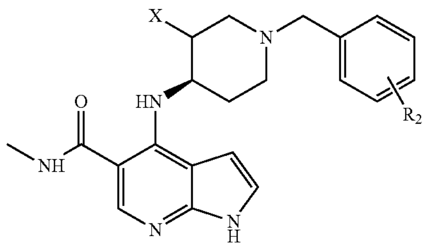

wherein X is halogen and $R_2$ is hydrogen, halogen, cyan or $C_1$-$C_3$ alkoxy, or a pharmaceutically acceptable salt thereof.

The present invention also provides a pharmaceutical composition for treating or preventing an autoimmune disease or cancer including the compound represented by Formula I or pharmaceutically acceptable salt thereof.

Effects of the Invention

The compound of the present invention can exhibit therapeutic effects on a variety of diseases, for example, inflammatory diseases, autoimmune diseases, myeloproliferative diseases, and human cancers due to its ability to regulate signal transduction at the level of JAK kinases. In particular, the compound of the present invention can exhibit better therapeutic effects on inflammatory diseases and autoimmune diseases at a low dose and with fewer side effects due to its high selectivity for JAK1.

BEST MODE FOR CARRYING OUT THE INVENTION

The present invention will now be described in detail.

One aspect of the present invention is directed to a compound represented by Formula I:

[Formula I]

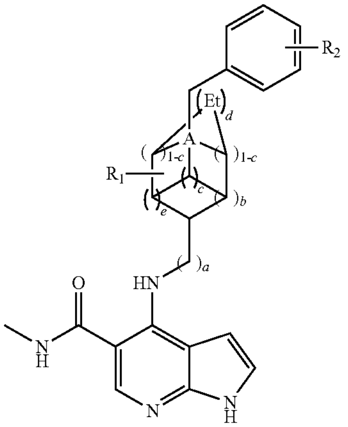

wherein $R_1$ is hydrogen, $C_1$-$C_3$ alkyl or halogen, $R_2$ is hydrogen, halogen, cyan or $C_1$-$C_3$ alkoxy, a and b are each independently an integer from 0 to 2, c and d are each independently an integer of 0 or 1 and satisfy the relationship c+d≤1, e is an integer of 1 or 2 and satisfies the relationship e≤3−b, A is a secondary or tertiary amine structurally capable of forming chemical bonds, and Et is ethyl, provided that when c or d is 1, b and e are all 1 (b=e=1), or a pharmaceutically acceptable salt thereof.

As will be understood with reference to Examples section that follows, it is preferrable that b and e are all 1, c is 0, d is 1, $R_1$ is hydrogen, and $R_2$ is chlorine or b and e are all 1, c is 0, d is 0, $R_1$ is methyl or fluorine, and $R_2$ is chlorine or methoxy.

The compound of the present invention may have one or more asymmetric centers. Unless otherwise indicated, all chiral (enantiomeric and diastereomeric) and racemic forms of the compound represented by Formulae I to IX are within the scope of the present invention. Many geometric isomers such as olefins, C═N double bonds, etc. may also exist in the compound and all stable isomers can be contemplated in the present invention. Cis and trans geometric isomers of the compound according to the present invention are described and may be isolated as a mixture of isomers or as separated isomeric forms. The compound of the present invention may be isolated in optically active or racemic forms. Methods for preparing optically active forms (for example, by resolution of racemic forms or by synthesis from optically active starting materials) are widely known in the art. All chiral (enantiomeric and diastereomeric), racemic forms and all geometric isomeric forms of a structure are intended, unless the specific stereochemistry or isomeric form is specifically indicated.

The compound represented by Formula I can regulate the activity of Janus kinases (JAKs). As used herein, the term "regulate" refers to the ability to increase or decrease the activity of one or more kinases of the JAK family. Due to this ability, the compound of the present invention or a composition including the compound can be brought into contact with JAKs to regulate the JAKs. Particularly, in some embodiments, the compound of the present invention may act as an inhibitor of one or more JAKs.

The compound of the present invention binds to and/or regulates JAKs, including any members of the JAK family. In some embodiments, the JAK is JAK1, JAK2, JAK3 or TYK2. In some embodiments, the JAK is JAK1 or JAK2. In some embodiments, the JAK is JAK1. In some embodiments, the JAK is JAK1 or JAK3.

Another aspect of the present invention is directed to a pharmaceutical composition for treating or preventing an autoimmune disease, an inflammatory disease or a cancer including the compound represented by Formula I or pharmaceutically acceptable salt thereof.

JAK-associated diseases include diseases, disorders, and conditions that are directly or indirectly associated with JAK expression or activity (for example, overexpression and/or aberrant activity). JAK-associated diseases may be, for example, diseases, disorders, and conditions that can be prevented, ameliorated or treated by regulation of JAK activity.

Examples of JAK-associated diseases include immune system-related diseases such as rejection reactions after organ transplantation (e.g., transplant rejection and graft versus host responses), multiple sclerosis, rheumatoid arthritis, juvenile arthritis, psoriatic arthritis, type I diabetes, lupus, psoriasis, inflammatory bowel disease, ulcerative colitis, Crohn's-disease, severe myasthenia gravis, immunoglobulin nephropathy, autoimmune thyroid disorders, asthma, food allergy, atopic dermatitis, psoriasis, and autoimmune bullous skin disorders such as pemphigus vulgaris (PV) and bullous pemphigoid (BP).

Other examples of JAK-associated diseases include inflammation and inflammatory diseases. Examples of inflammatory diseases include inflammatory diseases of the eye (e.g., iritis, uveitis, scleritis, conjunctivitis or related diseases), inflammatory diseases of the respiratory tract (e.g., rhinitis or sinusitis of the upper respiratory tract including the nose and sinuses and bronchitis and chronic obstructive pulmonary disease of the lower respiratory tract), inflammatory myopathy such as myocarditis, and other inflammatory diseases (e.g., systemic inflammatory response syndrome (SIRS) and septic shock.

Other examples of JAK-associated diseases include cancers characterized by solid tumors (e.g., prostate cancer, renal cancer, hepatic cancer, pancreatic cancer, gastric cancer, breast cancer, lung cancer, head and neck cancer, thyroid cancer, glioblastoma, Kaposi's sarcoma, Castleman's disease, and melanoma), hematologic cancers (e.g., lymphoma, leukemia such as acute lymphoblastic leukemia (ALL), multiple myeloma), and skin cancers such as cutaneous T-cell lymphoma (CTCL) and cutaneous B-cell lymphoma. Examples of cutaneous T-cell lymphomas include Sezary syndrome and mycosis fungoides.

The JAK inhibitor of the present invention can be used to treat a disease or condition associated with ischemic reperfusion injury or an inflammatory ischemic event such as stroke or cardiac arrest. The JAK inhibitor of the present invention can also be used to treat stenosis, sclerodermatitis or fibrosis.

The JAK inhibitor of the present invention can also be used to treat a condition associated with hypoxia or astrocytosis, for example, diabetic retinopathy, cancer or neurodegeneration. See Dudley, A. C. et al. Biochem. J. 2005, 390 (Pt 2):427-36 and Sriram, K. et al. J. Biol. Chem. 2004, 279(19): 19936-47. Epub 2004 Mar. 2. The JAK inhibitor of the present invention can also be used to treat Alzheimer's disease.

The JAK inhibitor of the present invention can also be used to treat gout and increased prostate size, for example, due to benign prostatic hyperplasia or prostatic hyperplasia.

The pharmaceutical composition of the present invention may be formulated into tablets, capsules (including sustained release or timed release preparations), pills, powders, granules, elixirs, tinctures, suspensions, syrups, and emulsions for oral administration. These preparations may also be administered intravenously (by bolus injection or infusion), intraperitoneally, subcutaneously or intramuscularly. All available dosage forms are well known to those skilled in the pharmaceutical art. The dosage forms can be administered alone but will generally be administered with a pharmaceutical carrier selected based on the chosen route of administration and standard pharmaceutical practice.

The pharmaceutical composition of the present invention may be administered intranasally through topical use of a suitable intranasal vehicle or via a transdermal route using a transdermal skin patch. To be administered in the form of a transdermal delivery system, the dosage administration will, of course, be continuous rather than intermittent throughout the dosage regimen.

The compounds that can be represented by Formula I are specifically exemplified in the following examples. The IC50 values of the compounds against JAK1, JAK2, and JAK3 were measured and the results are tabulated below. However, the specific examples of the compounds are given to provide complete disclosure of the invention and assist understanding of the invention by those skilled in the art and are not intended to limit the scope of the invention.

EXAMPLES

| Tofacitinib - Reference value | | | | | | | |
|---|---|---|---|---|---|---|---|
| | $IC_{50}$(μM) | | | | SELECTIVITY FOR JAK1 | | |
| | JAK1 | JAK2 | JAK3 | TYK2 | JAK2/JAK1 | JAK3/JAK1 | TYK2/JAK1 |
| TOFACITINIB | 0.0018 | 0.00423 | 0.00114 | 0.0101 | 2.34 | 0.63 | 5.61 |

Example 1—Piperidin-4-ylmethanamine Derivatives

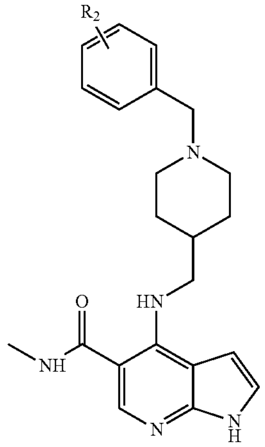

| | | $IC_{50}$(μM) | | | | Selectivity for JAK1 | | |
|---|---|---|---|---|---|---|---|---|
| | R2 | JAK1 | JAK2 | JAK3 | TYK2 | JAK2/JAK1 | JAK3/JAK1 | TYK2/JAK1 |
| 14a | H | 0.215 | — | — | — | — | — | — |
| 14b | 3-Cl | 0.243 | — | — | — | — | — | — |
| 14c | 4-Cl | 0.0722 | 0.712 | 0.426 | 0.0489 | 9.86 | 5.91 | 0.677 |
| 14d | 3-OMe | 0.132 | — | — | — | — | — | — |
| 14e | 4-OMe | 0.0934 | 1.08 | 0.576 | 0.200 | 11.6 | 6.16 | 2.14 |

Example 2—Aminopyrrolidine Derivatives

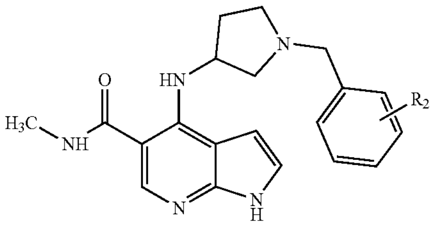

| | | $IC_{50}$(μM) | | | | Selectivity for JAK1 | | |
|---|---|---|---|---|---|---|---|---|
| | R2 | JAK1 | JAK2 | JAK3 | TYK2 | JAK2/JAK1 | JAK3/JAK1 | TYK2/JAK1 |
| 15a | H | 0.400 | — | — | — | — | — | — |
| 15b | 3-Cl | 0.0600 | — | — | — | — | — | — |
| 15c | 4-Cl | 0.0801 | — | — | — | — | — | — |
| 15d | 4-OMe | 0.827 | — | — | — | — | — | — |
| 15e | 3-OMe | 0.149 | — | — | — | — | — | — |
| 15f | 3-Cl | 0.0798 | 0.224 | 0.268 | 0.475 | 2.80 | 3.36 | 5.96 |
| 15g | 4-Cl | 0.0489 | 0.444 | 0.0702 | 0.485 | 9.07 | 1.44 | 9.92 |
| 15h | 3-Cl | 0.420 | — | — | — | — | — | — |
| 15i | 4-Cl | 0.703 | | | | | | |

Example 3—1,3-Cyclobutylamine Derivatives
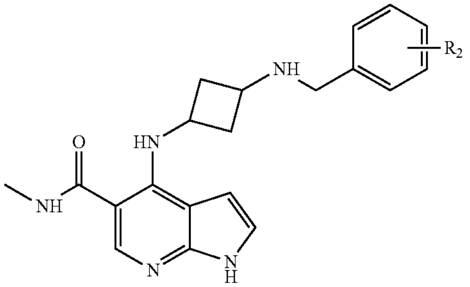
| | R2 | IC50(μM) JAK1 | JAK2 | JAK3 | TYK2 | Selectivity for JAK1 JAK2/JAK1 | JAK3/JAK1 | TYK2/JAK1 |
|---|---|---|---|---|---|---|---|---|
| 16a | H | 0.130 | — | — | — | — | — | — |
| 16b | 3-Cl | 0.0160 | — | — | — | — | — | — |
| 16c | 4-Cl | 0.0138 | 0.712 | 0.426 | 0.0489 | 9.86 | 5.91 | 0.677 |
| 16d | 4-OMe | 0.0814 | — | — | — | — | — | — |
Example 4—8-Azabicyclo[3.2.1]octan-3-amine derivatives
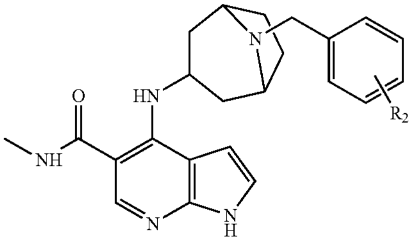
| | R2 | IC50(μM) JAK1 | JAK2 | JAK3 | TYK2 | Selectivity for JAK1 JAK2/JAK1 | JAK3/JAK1 | TYK2/JAK1 |
|---|---|---|---|---|---|---|---|---|
| 17a | H | 0.0749 | | | | | | |
| 17b | 3-Cl | 0.0408 | 0.153 | | 0.292 | 3.75 | | 7.18 |
| 17c | 4-Cl | 0.0174 | 2.59 | 0.0475 | 0.134 | 148 | 2.73 | 7.58 |
| 17d | 3-OMe | 0.0461 | 0.0899 | 0.225 | 0.0882 | 1.95 | 4.87 | 1.91 |
| 17e | 4-OMe | 0.0338 | 0.162 | 0.391 | 0.0791 | 4.89 | 11.6 | 2.34 |
| 17f | 3-CN | 0.00767 | 0.0588 | 0.0447 | 0.0922 | 7.66 | 5.83 | 12.0 |
| 17g | 4-CN | 0.0153 | 0.0866 | 0.0783 | 0.0961 | 5.65 | 5.11 | 6.17 |

Example 5—3-(S)-Aminopiperidine Derivatives

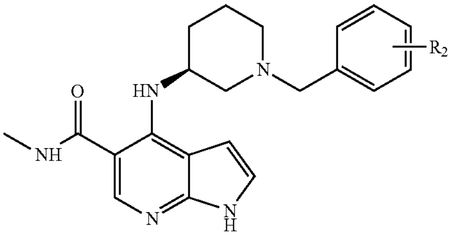

| | | IC$_{50}$(μM) | | | | Selectivity for JAK1 | | |
|---|---|---|---|---|---|---|---|---|
| | R2 | JAK1 | JAK2 | JAK3 | TYK2 | JAK2/JAK1 | JAK3/JAK1 | TYK2/JAK1 |
| 18a | 3-Cl | 1.87 | — | — | — | — | — | — |
| 18b | 3-OMe | 0.697 | 0.533 | 3.43 | 1.79 | 0.764 | 4.92 | 2.56 |

Example 6—4-Aminoazepane Derivatives

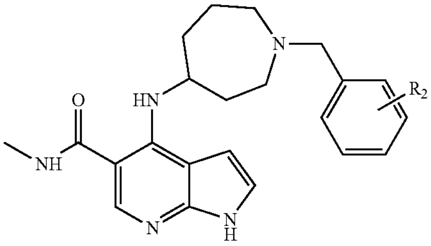

| | | IC$_{50}$(μM) | | | | Selectivity for JAK1 | | |
|---|---|---|---|---|---|---|---|---|
| | R2 | JAK1 | JAK2 | JAK3 | TYK2 | JAK2/JAK1 | JAK3/JAK1 | TYK2/JAK1 |
| 19a | H | 0.0377 | — | — | — | — | — | — |
| 19b | 3-Cl | 0.00943 | 0.0577 | 0.0625 | 0.0598 | 6.12 | 6.62 | 6.34 |
| 19c | 4-Cl | 0.0120 | 0.0443 | 0.0413 | 0.0494 | 3.69 | 3.44 | 4.11 |
| 19d | 4-OMe | 0.0305 | 0.175 | 0.283 | 0.0512 | 5.74 | 9.29 | 1.68 |
| 19e | 4-CN | 0.0327 | 0.150 | 0.343 | 0.120 | 4.58 | 10.5 | 3.35 |

Example 7—Trans-2-methylaminopiperidine Derivatives

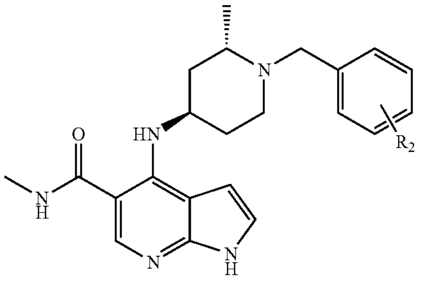

| | | IC$_{50}$(μM) | | | | Selectivity for JAK1 | | |
|---|---|---|---|---|---|---|---|---|
| | R2 | JAK1 | JAK2 | JAK3 | TYK2 | JAK2/JAK1 | JAK3/JAK1 | TYK2/JAK1 |
| 20a | H | 0.0106 | 0.179 | 0.025 | 0.276 | 16.9 | 2.36 | 26.1 |
| 20b | 3-Cl | 0.00112 | 0.0285 | 0.0196 | 0.0617 | 25.4 | 17.5 | 55.0 |
| 20c | 4-Cl | 0.00567 | 0.245 | 0.0245 | 0.1533 | 43.2 | 4.32 | 27.0 |

-continued
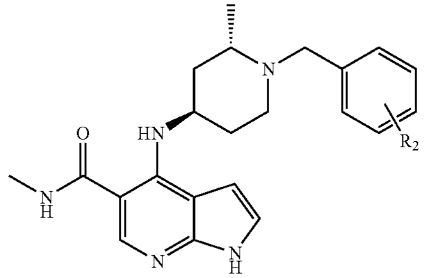
| | R2 | IC50(μM) JAK1 | JAK2 | JAK3 | TYK2 | Selectivity for JAK1 JAK2/JAK1 | JAK3/JAK1 | TYK2/JAK1 |
|---|---|---|---|---|---|---|---|---|
| 20d | 3-OMe | 0.00336 | 0.0885 | 0.0171 | 0.155 | 26.3 | 5.09 | 46.2 |
| 20e | 4-OMe | 0.0276 | 0.8174 | 0.0641 | 0.504 | 29.6 | 2.32 | 18.3 |
Example 8—Cis-2-methylaminopiperidine Derivatives
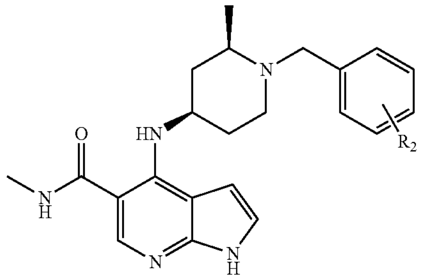
| | R2 | IC50(μM) JAK1 | JAK2 | JAK3 | TYK2 | Selectivity for JAK1 JAK2/JAK1 | JAK3/JAK1 | TYK2/JAK1 |
|---|---|---|---|---|---|---|---|---|
| 20f | 3-Cl | 0.00313 | 0.0088 | 0.0362 | 0.0486 | 2.82 | 11.6 | 15.5 |
| 20g | 4-Cl | 0.00013 | 0.0018 | 0.0034 | 0.0032 | 14.1 | 26.2 | 24.9 |
| 20h | 3-OMe | 0.0129 | 0.0284 | 0.0276 | 0.0795 | 2.21 | 2.14 | 6.18 |
| 20i | 4-OMe | 0.0238 | 0.0632 | 0.106 | 0.161 | 2.65 | 4.46 | 6.76 |
| 20j | 4-CN | 0.00193 | 0.0045 | 0.0024 | 0.0067 | 2.31 | 1.25 | 3.50 |

Example 9—3-Fluoroaminopiperidine Derivatives

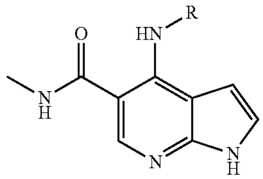

| | R | $IC_{50}$(μM) | | | | Selectivity for JAK1 | | |
|---|---|---|---|---|---|---|---|---|
| | | JAK1 | JAK2 | JAK3 | TYK2 | JAK2/JAK1 | JAK3/JAK1 | TYK2/JAK1 |
| 21a | 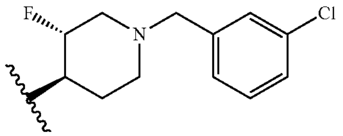 [SMILES: *[C@@H]1CCN(Cc2cccc(Cl)c2)C[C@H]1F] | 0.0170 | 0.0280 | 0.0092 | 0.308 | 1.65 | 0.545 | 18.2 |
| 21b | 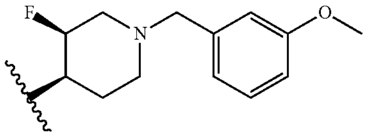 [SMILES: *[C@@H]1CCN(Cc2cccc(OC)c2)C[C@@H]1F] | 0.00077 | 0.0109 | 0.0887 | 0.116 | 14.1 | 115 | 150 |

Experimental Examples—Results of Cell-Based Assays on Janus Kinase Inhibitors

TABLE 1

| | $GI_{50}$(μM) | | | | Selectivity for JAK1 | | |
|---|---|---|---|---|---|---|---|
| | JAK1 | JAK2 | JAK3 | TYK2 | JAK2/JAK1 | JAK3/JAK1 | TYK2/JAK1 |
| Tofacitinib | 0.152 | 3.01 | 0.285 | 3.30 | 19.9 | 1.88 | 21.8 |
| | 0.129 | 0.409 | 0.451 | 0.150 | 3.17 | 3.49 | 1.16 |
| | 0.0669 | 0.143 | >10 | 0.233 | 2.14 | >100 | 3.49 |
| 17c | 1.17 | >10 | >10 | 3.42 | >10 | >10 | 2.92 |
| 19b | 0.472 | >10 | 7.98 | 4.21 | >20 | 16.9 | 8.93 |
| 20b | 0.390 | >10 | 8.24 | 5.34 | >25 | 21.1 | 13.7 |
| 20g | 0.0103 | >10 | 1.48 | 1.10 | >100 | 144 | 107 |
| 21b | 0.178 | >10 | >10 | 8.24 | >50 | >50 | 46.3 |

The inventive compounds that can be represented by Formula I, including the compounds exemplified above, can be prepared by various methods, including methods specifically described in the general synthetic procedures that follow. Those skilled in the art can estimate and understand synthetic methods for specific exemplary compounds and the compounds of Examples 1-9 based on the description of the general synthetic procedures, and thus explanations of individual methods for preparing the compounds are omitted.

[General Scheme I] - Experimental procedure for synthesis of intermediates 2 and 5-12

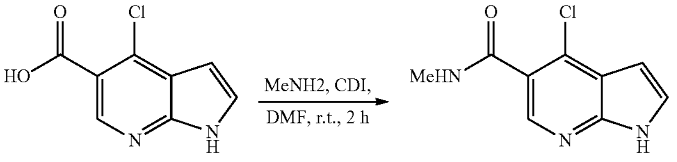

1 2

-continued
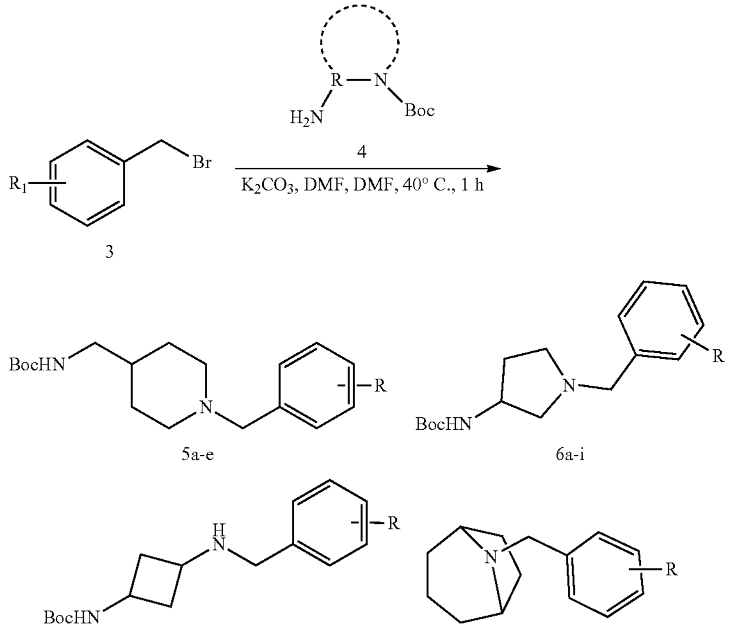
3
5a-e 6a-i
7a-d 8a-c
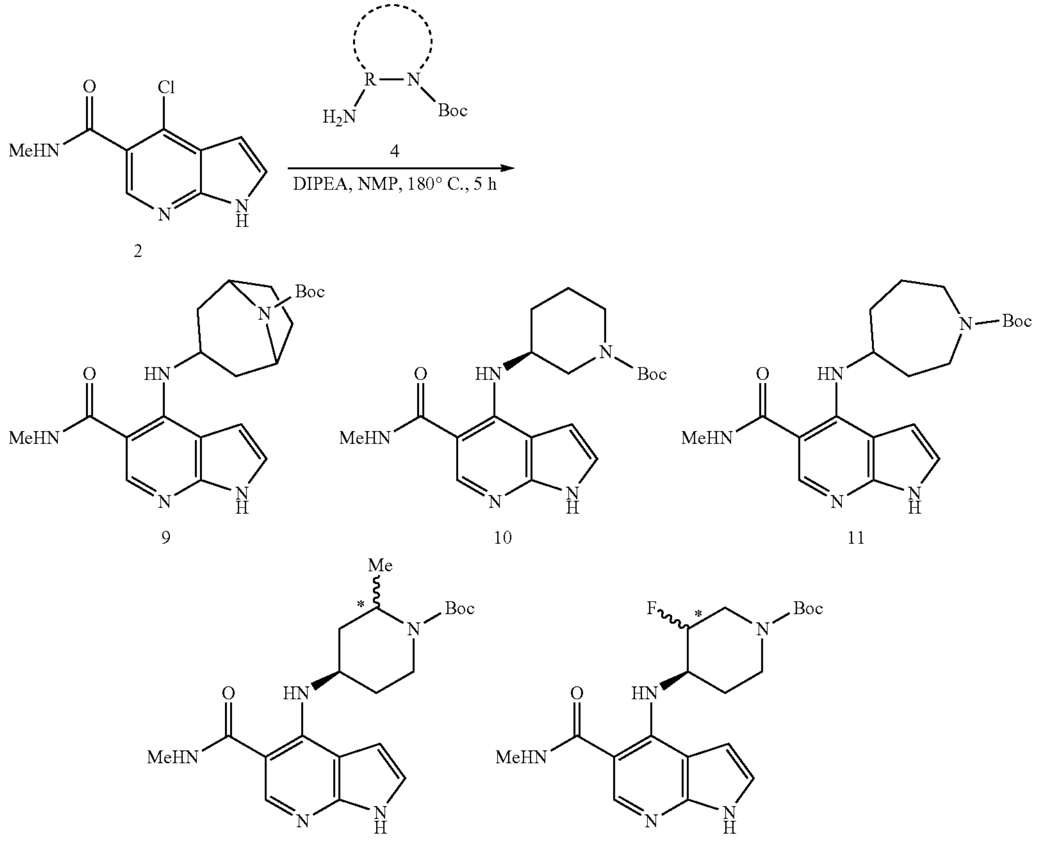
2
9 10 11
12a-b 13a-b

As depicted in General Scheme I, an N-alkylated 1-H-pyrrolo[2,3-b]pyridine carboxamide 2 was synthesized by carbonyldiimidazole-mediated amide coupling of 4-chloro-1H-pyrrolo[2,3-b]pyridine-5-carboxylic acid. Compounds 5-8 Were prepared from various Boc-protected amines by N-benzylation with $K_2CO_3$ as a base. Microwaves assisted nucleophilic substitution of chlorine with various amines at the C4-position of compound 2. To obtain desired products 13, 14, 15, and 16a-c, the amines were prepared in situ by treatment of modified Boc-protected intermediates 5-8 with HCl/MeOH. Alternatively, compound 2 was reacted with various Boc-protected amines to provide intermediates 9-13. In situ Boc-deprotection of 9-13 with HCl/MeOH and subsequent reductive amination with various benzaldehydes gave final products 16-20 in high yields.

General Scheme II - Experimental procedure for synthesis of final products

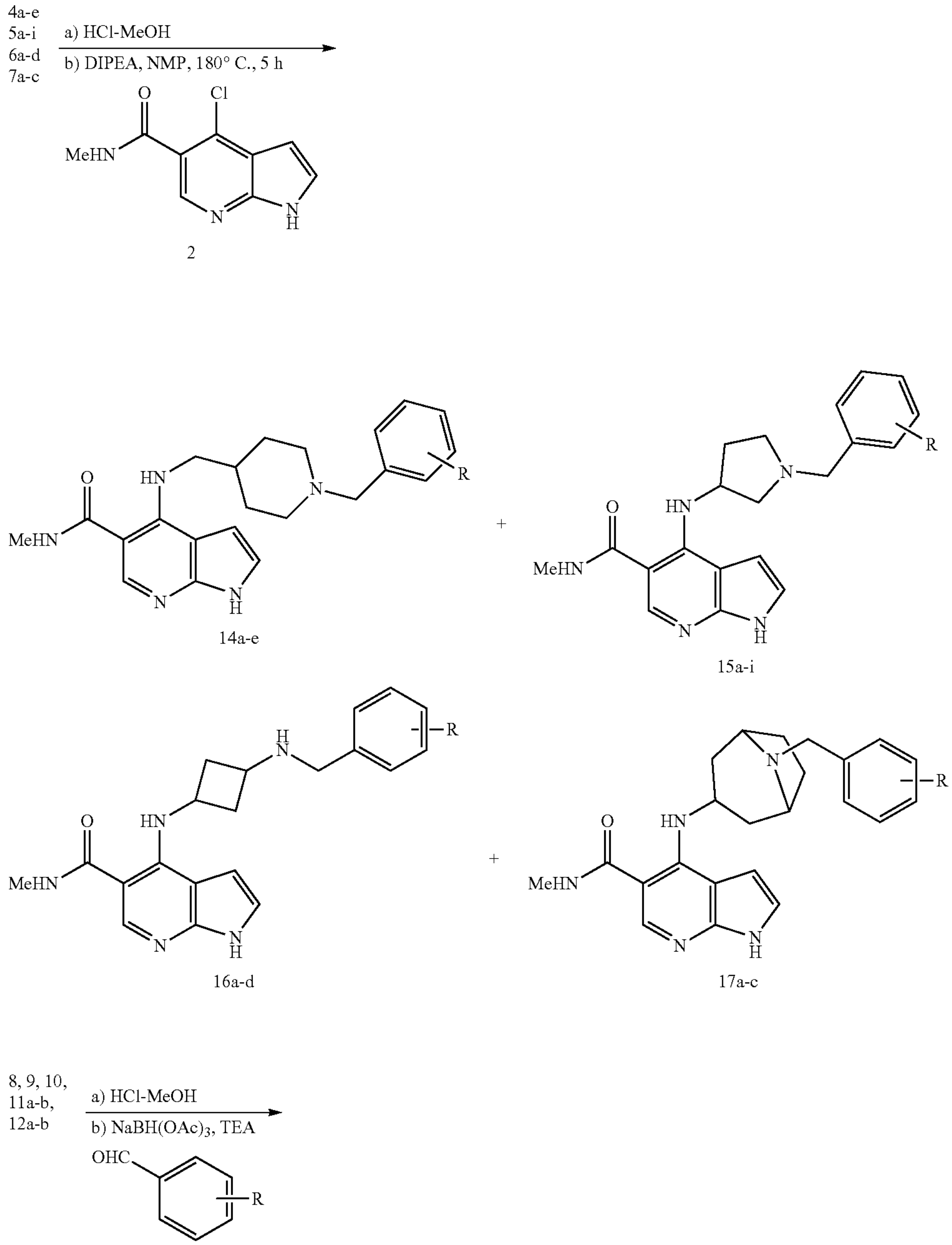

4a-e
5a-i
6a-d
7a-c

2

14a-e

+

15a-i 16a-d

+

17a-c 8, 9, 10,
11a-b,
12a-b

-continued

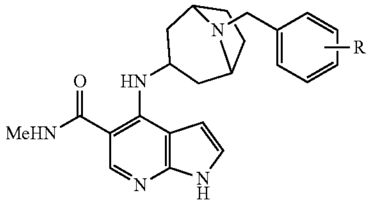

17d-g

+

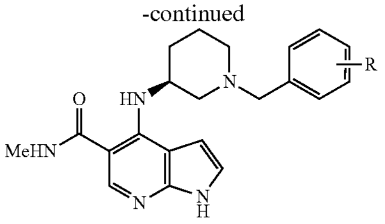

18a-b

+

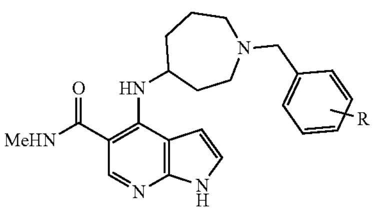

19a-e

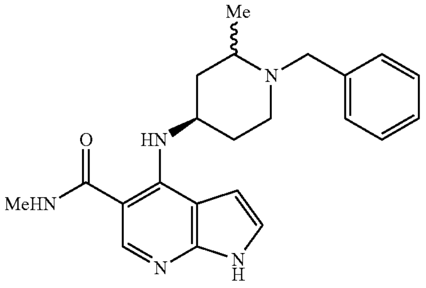

20a-j

+

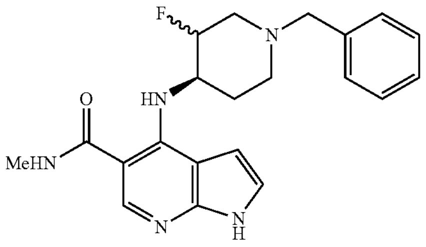

21a-b

General Procedure A

A 4-chloro-1H-pyrrolo[2,3-b]pyridine-5-carboxylic acid (1.05 g, 5.34 mmol) solution and CDI (0.963 g, 5.94 mmol) were added to DMF (20 ml) under a nitrogen atmosphere at room temperature. The mixture was stirred at the same temperature for 1 h. To the mixture was slowly added dropwise a 2.0 M methylamine (30.5 mmol) solution. The resulting mixture was stirred at room temperature for 1 h. The progress of the reaction was monitored by TLC and the DMF solvent was removed using a rotary evaporator. The resulting mixture was poured into ethyl acetate and the precipitate was collected by filtration. The precipitate was poured into water to remove the imidazole. Filtration afforded a product as a white solid.

4-Chloro-N-methyl-1H-pyrrolo[2,3-b]pyridine-5-carboxamide 2

The title compound was synthesized according to General procedure A. Yield: 86.5%. $^1$H NMR (400 MHz, DMSO-$d_6$) δ 12.15 (s, 1H), 8.37 (q, J=4.7 Hz, 1H), 8.24 (s, 1H), 7.65 (d, J=3.5 Hz, 1H), 6.56 (d, J=3.4 Hz, 1H), 2.80 (d, J=4.6 Hz, 3H). $^{13}$C NMR (101 MHz, Methanol-$d_4$) δ 168.9, 149.4, 143.1, 134.3, 128.5, 124.5, 120.7, 100.6, 26.9.

General Procedure B

To a solution of Boc-protected amine 4 (1.3 mmol) in DMF solvent (5 ml) were added $K_2CO_3$ (5.2 mmol) and benzyl bromide (2.6 mmol). The mixture was stirred at 40° C. for 1 h. The reaction mixture was poured into $Et_2O$ (40 ml), washed with $H_2O$ (40 ml), brine (40 ml), and dried over $MgSO_4$. The crude mixture was purified by silica gel flash chromatography (30% ethyl acetate in n-hexane elution) to afford a desired Boc-protected product.

tert-Butyl ((1-benzylpiperidin-4-yl)methyl)carbamate 5a

The title compound was synthesized according to General procedure B. Yield: 52.9%. $^1$H NMR (400 MHz, Chloroform-d) δ 7.30 (d, J=4.4 Hz, 3H), 7.27-7.21 (m, 2H), 4.57 (s, 1H), 3.48 (s, 2H), 3.01 (t, J=6.4 Hz, 2H), 2.88 (dt, J=11.5, 3.3 Hz, 2H), 1.94 (td, J=11.7, 2.5 Hz, 2H), 1.68-1.61 (m, 2H), 1.59 (s, 1H), 1.43 (s, 9H), 1.26 (qd, J=12.1, 3.9 Hz, 2H).

tert-Butyl ((1-(3-chlorobenzyl)piperidin-4-yl)methyl)carbamate 5b

The title compound was synthesized according to General procedure B. Yield: 78.8%. $^1$H NMR (400 MHz, Chloroform-d) δ 7.32 (dt, J=2.2, 1.0 Hz, 1H), 7.26 (s, 1H), 7.24-7.16 (m, 3H), 4.57 (s, 1H), 3.45 (s, 2H), 3.02 (t, J=6.4 Hz, 2H), 2.85 (d, J=11.3 Hz, 2H), 1.94 (td, J=11.6, 2.5 Hz, 2H), 1.65 (d, J=12.9 Hz, 2H), 1.57 (s, 1H), 1.44 (s, 9H), 1.32-1.21 (m, 2H).

tert-Butyl ((1-(3-4-chlorobenzyl)piperidin-4-yl)methyl)carbamate 5c

The title compound was synthesized according to General procedure B. Yield: 33.6%. $^1$H NMR (400 MHz, Chloroform-d) δ 7.27 (d, J=6.1 Hz, 2H), 7.23 (d, J=8.5 Hz, 2H), 4.57 (s, 1H), 3.44 (s, 2H), 3.01 (t, J=6.4 Hz, 2H), 2.84 (d, J=11.3 Hz, 2H), 1.97-1.88 (m, 2H), 1.65 (d, J=12.5 Hz, 2H), 1.56 (s, 1H), 1.43 (s, 9H), 1.31-1.19 (m, 2H).

tert-Butyl ((1-(3-methoxybenzyl)piperidin-4-yl)methyl)carbamate 5d

The title compound was synthesized according to General procedure B. Yield: 76.9%. $^1$H NMR (400 MHz, Chloroform-d) δ 7.21 (t, J=8.0 Hz, 1H), 6.91-6.87 (m, 2H), 6.80-6.77 (m, 1H), 4.57 (s, 1H), 3.81 (s, 3H), 3.46 (s, 2H), 3.01 (t, J=6.4 Hz, 2H), 2.88 (d, J=11.4 Hz, 2H), 1.98-1.89 (m, 2H), 1.64 (d, J=12.8 Hz, 2H), 1.57 (s, 1H), 1.43 (s, 9H), 1.32-1.21 (m, 2H).

tert-Butyl ((1-(4-methoxybenzyl)piperidin-4-yl)methyl)carbamate 5e

The title compound was synthesized according to General procedure B. Yield: 58.2%. $^1$H NMR (400 MHz, Chloroform-d) δ 7.23-7.18 (m, 2H), 6.87-6.82 (m, 2H), 4.56 (s, 1H), 3.80 (s, 3H), 3.42 (s, 2H), 3.01 (t, J=6.4 Hz, 2H), 2.87

(d, J=11.0 Hz, 2H), 1.91 (dd, J=12.5, 10.0 Hz, 2H), 1.64 (d, J=12.8 Hz, 2H), 1.56 (s, 1H), 1.43 (s, 9H), 1.31-1.19 (m, 2H).

tert-Butyl (1-benzylpyrrolidin-3-yl)carbamate 6a

The title compound was synthesized according to General procedure B. Yield: 68.3%. $^{1}$H NMR (400 MHz, Chloroform-d) δ 7.33-7.29 (m, 3H), 7.25-7.22 (m, 1H), 4.82 (s, 1H), 4.16 (s, 1H), 3.59 (s, 2H), 2.77 (s, 1H), 2.61 (t, J=8.1 Hz, 1H), 2.53 (s, 1H), 2.26 (dt, J=13.1, 7.9 Hz, 2H), 1.43 (s, 9H).

tert-Butyl (1-(3-chlorobenzyl)pyrrolidin-3-yl)carbamate 6b

The title compound was synthesized according to General procedure B. Yield: 95.5%. $^{1}$H NMR (400 MHz, Chloroform-A) δ 7.32 (s, 1H), 7.25-7.20 (m, 2H), 7.18 (t, J=4.1 Hz, 1H), 4.80 (s, 1H), 4.17 (s, 1H), 3.62-3.50 (m, 2H), 2.77 (s, 1H), 2.61 (t, J=8.1 Hz, 1H), 2.53 (s, 1H), 2.27 (q, J=13.5, 11.1 Hz, 2H), 1.58 (d, J=9.1 Hz, 2H), 1.44 (s, 11H).

tert-Butyl (1-(4-chlorobenzyl)pyrrolidin-3-yl)carbamate 6c

The title compound was synthesized according to General procedure B. Yield: 31.8%. $^{1}$H NMR (400 MHz, Chloroform-d) δ 7.30-7.28 (m, 1H), 7.27 (d, J=2.2 Hz, 1H), 7.24 (d, J=2.4 Hz, 1H), 7.23-7.22 (m, 1H), 4.79 (s, 1H), 4.16 (s, 1H), 3.55 (s, 2H), 2.75 (s, 1H), 2.59 (dd, J=9.7, 6.4 Hz, 1H), 2.50 (d, J=9.6 Hz, 1H), 2.27 (td, J=15.2, 13.9, 6.3 Hz, 2H), 1.66-1.53 (m, 1H); 1.43 (s, 9H).

tert-Butyl (1-(3-methoxybenzyl)pyrrolidin-3-yl)carbamate 6d

The title compound was synthesized according to General procedure B. Yield: 62.9%. $^{1}$H NMR (400 MHz, Chloroform-d) δ 7.25-7.19 (m, 1H), 6.91-6.86 (m, 2H), 6.81-6.77 (m, 1H), 4.82 (s, 1H), 4.15 (d, J=13.1 Hz, 1H), 3.81 (s, 3H), 3.57 (s, 2H), 2.78 (s, 1H), 2.60 (t, J=8.1 Hz, 1H), 2.52 (d, J=9.7 Hz, 1H), 2.37-2.18 (m, 2H), 1.67-1:53 (m, 2H), 1.43 (s, 9H).

tert-Butyl (1-(4-methoxybenzyl)pyrrolidin-3-yl)carbamate 6e

The title compound was synthesized according to General procedure B. Yield: 57.6%. $^{1}$H NMR (400 MHz, Chloroform-d) δ 7.23-7.19 (m, 2H), 6.87-6.83 (m, 2H), 4.80 (s, 1H), 4.15 (s, 1H), 3.80 (s, 3H), 3.53 (s, 2H), 2.76 (d, J=11.3 Hz, 1H), 2.63-2.55 (m, 1H), 2.49 (d, J=9.7 Hz, 1H), 2.34-2.19 (m, 2H), 1.72-1.49 (m, 2H), 1.43 (s, 9H).

tert-Butyl (R)-(1-(3-chlorobenzyl)pyrrolidin-3-yl) carbamate 6f

The title compound was synthesized according to General procedure B. Yield: 85.2%. $^{1}$H NMR (400 MHz, Chloroform-d) δ 7.32 (d, J=2.0 Hz, 1H), 7.25-7.19 (m, 2H), 7.18 (ddd, J=6.2, 2.8, 1.6 Hz, 1H), 4.82 (s, 1H), 4.17 (s, 1H), 3.61-3.51 (m, 2H), 2.77 (s, 1H), 2.60 (t, J=8.1 Hz, 1H), 2.52 (d, J=9.6 Hz, 1H), 2.34-2.20 (m, 2H), 1.64-1.53 (m, 1H), 1.44 (s, 9H).

tert-Butyl (R)-(1-(4-chlorobenzyl)pyrrolidin-3-yl) carbamate 6g

The title compound was synthesized according to General procedure B. Yield: 66.4%. $^{1}$H NMR (400 MHz, Chloroform-d) δ 7.30-7.26 (m, 2H), 7.26-7.22 (m, 2H), 4.81 (s, 1H), 4.16 (s, 1H), 3.55 (s, 2H), 2.76 (d, J=9.7 Hz, 1H), 2.59 (dd, J=9.7, 6.4 Hz, 1H), 2.50 (d, J=9.7 Hz, 1H), 2.33-2.20 (m, 2H), 1.61-1.54 (m, 1H), 1.43 (s, 9H).

tert-Butyl (S)-(1-(3-chlorobenzyl)pyrrolidin-3-yl) carbamate 6h

The title compound was synthesized according to General procedure B. Yield: 78.3%. $^{1}$H NMR (400 MHz, Chloroform-d) δ 7.3 (s, 1H), 7.2-7.2 (m, 3H), 4.8 (s, 1H), 4.1 (dd, J=14.9, 7.7 Hz, 1H), 3.6-3.5 (m, 2H), 2.8 (s, 1H), 2.7-2.6 (m, 1H), 2.5 (d, J=8.1 Hz, 1H), 2.3-2.2 (m, 2H), 1.6 (d, J=2.5 Hz, 1H), 1.4 (s, 9H).

tert-Butyl (S)-(1-(4-chlorobenzyl)pyrrolidin-3-yl) carbamate 6i

The title compound was synthesized according to General procedure B. Yield: 78.9%. $^{1}$H NMR (400 MHz, Chloroform-d) δ 7.3 (d, J=8.6 Hz, 2H), 7.3-7.2 (m, 2H), 4.8 (s, 1H), 4.2-4.1 (m, 1H), 3.5 (s, 2H), 2.8 (s, 1H), 2.6 (dd, J=9.6, 6.5 Hz, 1H); 2.5 (d, J=8.0 Hz, 1H), 2.3 (td, J=14.4, 13.8, 6.0 Hz, 2H), 1.6-1.5 (m, 1H), 1.4 (s, 9H).

tert-Butyl (3-(benzylamino)cyclobutyl)carbamate 7a

The title compound was synthesized according to General procedure B. Yield: 34.4% (trans:cis=2.5:1) $^{1}$H NMR (400 MHz, Chloroform-d) δ 7.3-7.3 (m, 4H), 7.3-7.2 (m, 1H), 4.7 (s, 1H), 4.2 (s, 1H), 3.8 (d, J=2.6 Hz, 2H), 3.5-3.4 (m, 1H), 3.1-2.9 (m, 1H), 2.7-2.6 (m, 2H), 2.2-2.0 (m, 2H), 1.4 (s, 9H).

tert-Butyl (3-((3-chlorobenzyl)amino)cyclobutyl)carbamate 7b

The title compound was synthesized according to General procedure B: Yield: 44.3% (trans:cis=2.2:1) $^{1}$H NMR (400 MHz, Chloroform-d) δ 7.3-7.2 (m, 4H), 4.7 (s, 1H), 4.2 (d, J=22.1 Hz, 1H), 3.7 (s, 2H), 3.4 (m, 1H), 2.7-2.6 (m, 2H), 2.2-2.0 (m, 2H), 1.4 (s, 14H).

tert-Butyl (3-((4-chlorobenzylamino)cyclobutyl)carbamate 7c

The title compound was synthesized according to General procedure B. Yield: 33.2% (trans:cis=2.5:1) $^{1}$H NMR (400 MHz, Chloroform-d) δ 7.3-7.3 (m, 2H), 7.2 (t, J=0.9, 0.2 Hz, 2H), 4.7 (s, 1H) 4.2 (d, J=28.2 Hz, 1H), 3.7 (s, 2H), 3.7 (s, 2H), 3.4-3.3 (m, 1H), 2.7-2.6 (m, 2H), 2.1-2.0 (m, 2H), 1.4 (s, 9H).

tert-Butyl (3-((4-methoxybenzyl)amino)cyclobutyl)carbamate 7d

Yield: 34.4%. $^{1}$HNMR (400 MHz, Chloroform-d) trans:cis=3:1 δ 7.24-7.18 (m, 8H), 6.87-6.82 (m, 8H), 4.70 (s, 1H), 4.66-4.57 (m, 3H), 4.17 (d, J=14.6 Hz, 1H), 3.82 (d, J=0.9 Hz, 3H), 3.80 (s, 12H), 3.63 (d, J=4.0 Hz, 8H), 3.44-3.37 (m, 1H), 2.98 (tt, J=8.4, 6.7 Hz, 3H), 2.71-2.62 (m, 6H), 2.20-2.04 (m, 1H), 1.59-1.45 (m, 16H), 1.43 (d, J=2.9 Hz, 36H).

tert-Butyl (8-benzyl-8-azabicyclo[3.2.1]octan-3-yl) carbamate 8a

Commercial available tert-Butyl (8-(3-chlorobenzyl)-8-azabicyclo[3.2.1] octan-3-yl)carbamate 8b

The title compound was synthesized according to General procedure B. Yield: 54.6%; $^{1}$H NMR (400 MHz, Chloroform-d) δ 7.39 (dt, J=2.3, 1.1 Hz, 1H), 7.24-7.19 (m, 3H), 4.32 (s, 1H), 3.80 (s, 1H), 3.50 (s, 2H), 3.17 (p, J=3.0 Hz, 2H), 2.05-1.95 (m, 2H), 1.86-1.78 (m, 2H), 1.70 (d, J=8.1 Hz, 2H), 1.53-1.46 (m, 2H), 1.44 (s, 9H).

tert-Butyl (8-(4-chlorobenzyl)-8-azabicyclo[3.2.1] octan-3-yl)carbamate 8c

The title compound was synthesized according to General procedure B. Yield: 69.3%; $^{1}$H NMR (400 MHz, Chloroform-d) δ 7.31-7.27 (m, 4H), 4.35-4.27 (m, 1H), 3.81 (d, J=14.8 Hz, 1H), 3.48 (s, 2H), 3.17 (q, J=3.7, 3.2 Hz, 2H), 2.00 (m, J=7.1, 2.9 Hz, 2H), 1.81 (m, J=12.1, 5.3, 2.7 Hz, 2H), 1.74-1.65 (m, 2H), 1.47 (dd, J=12.3, 2.7 Hz, 2H), 1.43 (s, 9H).

General Procedure C

DIEA (2 eq) and 4-chloro-N-alkyl-1H-pyrrolo[2,3-b]pyridine-5-carboxamide (1.0 mmol) were added to a solution of amine (2 eq) in NMP (2 ml). The mixture was stirred under microwave irradiation at 180° C. for 5 h. The resulting mixture was cooled to room temperature, diluted with ethyl acetate, washed with $H_2O$ and brine, and dried over $MgSO_4$. The crude mixture was purified by silica gel flash chromatography (dichloromethane:MeOH=10:1 elution) to afford a title product 9-13.

tert-Butyl 3-((5-(methylcarbamoyl)-1H-pyrrolo[2,3-b]pyridin-4-yl)amino)-8-azabicyclo[3.2.1]octane-8-carboxylate 9

The title compound was synthesized according to General procedure C. Yield: 50.5% (endo exo 1:1) $^{1}$H NMR (400 MHz, Chloroform-d) δ 9.8 (d, J=7.4 Hz, 1H), 9.0 (d, J=8.5 Hz, 1H), 8.2 (d, J=6.0 Hz, 2H), 7.1 (d, J=3.6 Hz, 1H), 7.0 (d, J=3.7 Hz, 1H), 6.6 (d, J=3.7 Hz, 1H), 6.5 (d, J=3.7 Hz, 1H), 6.2 (s, 2H), 4.6-4.4 (m, 1H), 4.4-4.3 (m, 1H), 4.3 (s, 4H), 3.0 (dd, J=6.2, 4.8 Hz, 6H), 2.4 (d, J=7.7 Hz, 2H), 2.2-2.1 (m, 8H), 1.9 (d, J=14.1 Hz, 3H), 1.8 (t, J=7.1 Hz, 3H), 1.5 (s, 9H), 1.5 (s, 9H).

tert-Butyl (R)-3-((5-(methylcarbamoyl)-1H-pyrrolo [2,3-b]pyridin-4-yl)amino)piperidine-1-carboxylate 10

The title compound was synthesized according to General procedure C. Yield: 54.1%; $^{1}$H NMR (400 MHz, Chloroform-d) δ 9.7 (s, 1H), 9.2 (d, J=6.6 Hz, 1H), 8.2 (s, 1H), 7.1 (d, J=3.7 Hz, 1H), 6.7 (s, 1H), 6.1 (s, 1H), 4.3 (dd, J=13.2, 3.8 Hz, 1H), 4.0 (s, 2H), 3.0 (d, J=4.8 Hz, 3H), 2.9 (d, J=9.2 Hz, 2H), 1.9-1.6 (m, 4H), 1.4 (s, 9H).

tert-Butyl 4-((5-(methylcarbamoyl)-1H-pyrrolo[2,3-b]pyridin-4-yl)amino)azepane-1-carboxylate 11

The title compound was synthesized according to General procedure C. Yield: 38.1%. $^{1}$H NMR (400 MHz, Methanol-$d_4$) δ 8.19 (d, J=1.9 Hz, 1H), 7.11 (d, J=3.6 Hz, 1H), 6.64 (t, J=4.1 Hz, 1H), 4.27-4.19 (m, 1H), 3.61-3.39 (m, 4H), 2.87 (d, J=1.1 Hz, 3H), 2.29-2.19 (m, 1H), 2.09 (d, J=12.5 Hz, 1H), 1.97-1.65 (m, 4H), 1.50 (s, 9H).

tert-Butyl trans-2-methyl-4-((5-(methylcarbamoyl)-1H-pyrrolo[2,3-b]pyridin-4-yl)amino)piperidine-1-carboxylate 12a The title compound was synthesized according to General procedure C. Yield: 54.1%. $^{1}$H NMR (400 MHz, Chloroform-d) δ 9.99 (s, 1H), 9.08 (d, J=7.9 Hz, 1H), 8.23 (s, 1H), 7.07 (d, J=3.6 Hz, 1H), 6.57 (d, J=0.3.7 Hz, 1H), 6.17 (s, 1H), 4.56 (s, 1H), 4.33-4.23 (m, 1H), 4.12 (d, J=13.8 Hz, 1H), 2.98 (d, J=4.7 Hz, 4H), 2.19-2.05 (m, 2H), 1.74-1.62 (m, 1H), 1.48 (s, 10H), 1.30 (d, J=7.0 Hz, 3H). $^{13}$C NMR (101 MHz, Methanol-$d_4$) δ 172.5, 156.3, 150.7, 150.6, 144.9, 123.0, 106.6, 105.0, 103.1, 81.1, 47.5, 38.9, 34.6, 28.7, 26.6, 16.8.

tert-Butyl (2R,4R)-2-methyl-4-((5-(methylcarbamoyl)-1H-pyrrolo[2,3-b]pyridin-4-yl)amino)piperidine-1-carboxylate 12b The title compound was synthesized according to General procedure C. Yield: 46.8%; $^{1}$H NMR (400 MHz, Chloroform-d) δ 8.15 (s, 1H), 7.35 (s, 2H), 7.06 (d, J=3.7 Hz, 1H), 6.52 (d, J=3.7 Hz, 1H), 4.38 (p, J=4.5 Hz, 1H), 4.32-4.23 (m, 1H), 4.00-3.92 (m, 1H), 3.31 (dd, 1H), 2.94 (s, 3H), 2.10-1.98 (m, 2H), 1.96-1.84 (m, 2H), 1.48 (s, 9H), 1.27 (d, J=7.1 Hz, 3H).

tert-Butyl trans-3-fluoro-4-((5-(methylcarbamoyl)-1H-pyrrolo[2,3-b]pyridin-4-yl)amino)piperidine-1-carboxylate 13a The title compound was synthesized according to General procedure C. Yield: 30.5%, $^{1}$H NMR (400 MHz, Chloroform-d) δ 9.99 (s, 1H), 9.08 (d, J=7.9 Hz, 1H), 8.23 (s, 1H), 7.07 (d, J=3.6 Hz, 1H), 6.57 (d, J=3.7 Hz, 1H), 6.17 (s, 1H), 4.56 (s, 1H), 4.33-4.23 (m, 1H), 4.12 (d, J=13.8 Hz, 1H), 2.98 (d, J=4.7 Hz, 4H), 2.19-2.05 (m, 2H), 1.74-1.62 (m, 1H), 1.48 (s, 10H), 1.30 (d, J=7.0 Hz, 3H).

tert-Butyl (3S,4R)-3-fluoro-4-((5-(methylcarbamoyl)-1H-pyrrolo[2,3-b]pyridin-4-yl)amino)piperidine-1-carboxylate 13b The title compound was synthesized according to General procedure C. Yield: 28.7%; $^{1}$H NMR (400 MHz, Chloroform-d) δ 9.64 (s, 1H), 9.48 (d, J=8.4 Hz, 1H), 8.25 (s, 1H), 7.10 (d, J=3.7 Hz, 1H), 6.45 (d, J=3.7 Hz, 1H), 6.08 (s, 1H), 5.30 (d, J=0.4 Hz, 1H), 4.85 (d, J=48.3 Hz, 1H), 4.44 (s, 1H), 4.23 (dt, J=25.0, 8.1 Hz, 2H), 3.00 (d, J=4.8 Hz, 43H), 2.96 (s, 1H), 2.01 (q, J=7.5, 6.4 Hz, 2H), 1.48 (s, 9H).

General Procedure D

4 N HCl in dioxane (2 mL) was added to a solution of compound 5-8 in MeOH. The mixture was stirred at room temperature for 1 h for in situ Boc deprotection. After evaporation and further drying under high vacuum, the resulting product was used in the next step without further purification.

DIEA (2 eq) and 4-chloro-N-alkyl-1H-pyrrolo[2,3-b]pyridine-5-carboxamide (0.5 mmol) were added to a solution of the Boc-deprotected amine hydrochloride in NMP (2 ml). The mixture was stirred under microwave irradiation at 180° C. for 5 h. The resulting mixture was cooled to room temperature, diluted with ethyl acetate, washed with $H_2O$ and brine, and dried over $MgSO_4$. The crude mixture was purified by silica gel flash chromatography (dichloromethane:MeOH=10:1 elution) to afford a title product 14a-e, 15a-i, 16a-d, 17a-c.

4-(((1-Benzylpiperidin-4-yl)methyl)amino)-N-methyl-1H-pyrrolo[2,3-b]pyridine-5-carboxamide 14a The title compound was synthesized according to General procedure D. Yield: 30.6%; $^1$H NMR (400 MHz, Methanol-$d_4$) δ 8.17 (s, 1H), 7.35-7.32 (m, 3H), 7.33-7.26 (m, 1H), 7.08 (d, J=3.7 Hz, 1H), 6.69 (d, J=3.7 Hz, 1H), 3.62 (d, J=5.6 Hz, 4H), 3.03 (d, J=11.7 Hz, 2H), 2.86 (s, 3H), 2.17 (t, J=11.9 Hz, 2H), 1.92 (d, J=13.2 Hz, 2H), 1.82-1.70 (m, 1H), 1.50-1.38 (m, 2H); $^{13}$C NMR (101 MHz, Methanol-$d_4$) δ 171.7, 151.4, 149.7, 144.1, 136.1, 130.4, 128.8, 128.2, 121.6, 106.4, 103.9, 103.0, 63.4, 53.4, 50.7, 36.6, 29.7, 26.6; HRMS (ESI, m/z) calculated for $C_{22}H_{28}N_5O$ [M+H]$^+$ 378.2288 found 378.2293.

4-(((1-(3-Chlorobenzyl)piperidin-4-yl)methyl)amino)-N-methyl-1H-pyrrolo[2,3-b]pyridine-5-carboxamide 14b The title compound was synthesized according to General procedure D. Yield: 52.0%; $^1$H NMR (400 MHz, DMSO-$d_6$) δ 11.43 (s, 1H), 9.38 (t, J=5.4 Hz, 1H), 8.27 (s, 1H), 8.19 (d, J=4.7 Hz, 1H), 7.40-7.24 (m, 4H), 7.10 (dd, J=3.6, 2.4 Hz, 1H), 6.60 (dd, J=3.6, 1.9 Hz, 1H), 3.55-3.45 (m, 4H), 2.84 (d, J=11.1 Hz, 2H), 2.73 (d, J=4.4 Hz, 3H), 1.97 (s, 2H), 1.80-1.73 (m, 2H), 1.61 (s, 1H), 1.32 (q, J=10.8 Hz, 2H); $^{13}$C NMR (101 MHz, DMSO-$d_6$) δ 170.2, 150.2, 150.1, 144.4, 132.9, 130.0, 128.4, 127.4, 126.9, 121.3, 105.1, 102.5, 101.9, 61.3, 52.7, 49.7, 36.0, 29.4, 26.0; HRMS (ESI, m/z) calculated for $C_{22}H_{27}ClN_5O$ [M+H]$^+$ 412.1899 found 412.1901.

4-(((1-(4-Chlorobenzyl)piperidin-4-yl)methyl)amino)-N-methyl-1H-pyrrolo[2,3-b]pyridine-5-carboxamide 14c The title compound was synthesized according to General procedure D. Yield: 18.8%; $^1$H NMR (400 MHz, Methanol-$d_4$) δ 8.18 (s, 1H), 7.39 (s, 4H), 7.09 (d, J=3.6 Hz, 1H), 6.70 (d, J=3.7 Hz, 1H), 3.84-3.77 (m, 2H), 3.63 (d, J=6.7 Hz, 2H), 3.20-3.11 (m, 2H), 2.87 (s, 3H), 2.43 (s, 2H), 2.02-1.95 (m, 2H), 1.55-1.43 (m, 2H); $^{13}$C NMR (101 MHz, Methanol-$d_4$) δ 171.1, 151.4, 148.3, 142.9, 134.6, 131.9, 129.1, 121.7, 106.4, 103.9, 103.0, 61.7, 53.0, 50.3, 35.9, 29.0, 26.5; HRMS (ESI, m/z) calculated for $C_{22}H_{27}ClN_5O$ [M+H]$^+$ 412.1899 found 412.1901.

4-(((1-(3-Methoxybenzyl)piperidin-4-yl)methyl)amino)-N-methyl-1H-pyrrolo[2,3-b]pyridine-5-carboxamide 14d The title compound was synthesized according to General procedure D. Yield: 17.3%; $^1$H NMR (400 MHz, Methanol-$d_4$) δ 8.18 (s, 1H), 7.25 (dd, J=8.2, 7.5 Hz, 1H), 7.08 (d, J=3.7 Hz, 1H), 6.96-6.85 (m, 3H), 6.69 (d, J=3.7 Hz, 1H), 3.80 (s, 3H), 3.64-3.58 (m, 4H), 3.05 (d, J=11.7 Hz, 2H), 2.86 (s, 3H), 2.22 (t, J=11.9 Hz, 2H), 1.93 (d, J=13.2 Hz, 2H), 1.84-1.72 (m, 1H), 1.45 (q, J=12.5, 3.8 Hz, 2H); $^{13}$C NMR (101 MHz, Methanol-$d_4$) δ 171.5, 160.1, 151.3, 149.5, 143.9, 137.5, 129.7, 122.6, 121.6, 115.7, 113.7, 106.4, 103.9, 103.0, 63.2, 55.5, 53.4, 50.6, 36.4, 29.6, 26.5; HRMS (ESI, m/z) calculated for $C_{23}H_{30}N_5O_2$ [M+H]$^+$ 408.2394 found 408.2392.

4-(((1-(4-Methoxybenzyl)piperidin-4-yl)methyl)amino)-N-methyl-1H-pyrrolo[2,3-b]pyridine-5-carboxamide 14e The title compound was synthesized according to General procedure D. Yield: 39.7%; $^1$H NMR (400 MHz, DMSO-$d_6$) δ 8.13 (s, 1H), 7.25-7.20 (m, 2H), 7.09 (d, J=3.6 Hz, 1H), 6.89-6.84 (m, 2H), 6.61 (d, J=3.7 Hz, 1H), 3.69 (s, 3H), 3.57 (s, 2H), 3.46 (d, J=6.5 Hz, 2H), 2.92 (d, J=11.3 Hz, 2H), 2.70 (s, 3H), 2.16 (s, 2H), 1.76 (d, J=13.1 Hz, 2H), 1.64 (s, 1H), 1.30 (q, J=12.3 Hz, 2H); $^{13}$C NMR (101 MHz, Methanol-$d_4$) δ 172.0, 160.4, 151.5, 150.0, 144.4, 132.2, 122.0, 114.5, 106.6, 104.1, 103.0, 62.4, 55.6, 53.2, 50.6, 36.4, 29.4, 26.6; HRMS (ESI, m/z) calculated for $C_{23}H_{30}N_5O_2$ [M+H]$^+$ 408.2394 found 408.2392.

4-((1-Benzylpyrrolidin-3-yl)amino)-N-methyl-1H-pyrrolo[2,3-b]pyridine-5-carboxamide 15a The title compound was synthesized according to General procedure D. Yield: 1.56%; $^1$H NMR (400 MHz, Methanol-$d_4$) δ 8.18 (s, 1H), 7.40-7.23 (m, 5H), 7.10 (d, J=3.7 Hz, 1H), 6.64 (d, J=3.7 Hz, 1H), 4.77-4.70 (m, 1H), 3.74 (d, J=1.7 Hz, 2H), 3.05 (dd, J=10.1, 6.5 Hz, 1H), 2.88 (s, 3H), 2.86 (d, J=10.0 Hz, 1H), 2.72-2.63 (m, 2H), 2.51-2.41 (m, 0.1H), 1.90-1.79 (m, 1H); $^{13}$C NMR (101 MHz, Methanol-$d_4$) δ 171.9, 150.4, 149.9, 144.3, 138.1, 129.7, 129.0, 128.1, 122.3, 106.3, 104.5, 102.6, 62.3, 60.8, 53.4, 53.3, 49.7, 49.5, 49.3, 49.0, 48.8, 48.6, 48.4, 34.3, 26.6; HRMS (ESI, m/z) calculated for $C_{20}H_{24}N_5O$ [M+H]$^+$ 350.1975 found 350.1979.

4-((1-(3-Chlorobenzyl)pyrrolidin-3-yl)amino)-N-methyl-1H-pyrrolo[2,3-b]pyridine-5-carboxamide 15b The title compound was synthesized according to General procedure D. Yield: 11.7%; $^1$H NMR (400 MHz, Methanol-$d_4$) δ 8.19 (s, 1H), 7.43 (q, J=1.4 Hz, 1H), 7.32-7.29 (m, 2H), 7.28-7.24 (m, 1H), 7.10 (d, J=3.7 Hz, 1H), 6.65 (d, J=3.7 Hz, 1H), 4.75-4.69 (m, 1H), 3.72 (s, 2H), 3.02-2.95 (m, 1H), 2.89 (s, 3H), 2.88-2.84 (m, 1H), 2.73-2.68 (m, 1H), 2.62 (td, J=8.8, 6.1 Hz, 1H), 2.50-2.41 (m, 1H), 1.90-1.80 (m, 1H); HRMS (ESI, m/z) calculated for $C_{20}H_{23}ClN_5O$ [M+H]$^+$ 384.1586 found 384.1588.

4-((1-(4-Chlorobenzyl)pyrrolidin-3-yl)amino)-N-methyl-1H-pyrrolo[2,3-b]pyridine-5-carboxamide 15c The title compound was synthesized according to General procedure D. Yield: 34.4%; $^1$H NMR (400 MHz, Methanol-$d_4$) δ 8.18 (s, 1H), 7.40-7.30 (m, 4H), 7.10 (d, J=3.7 Hz, 1H), 6.64 (d, J=3.7 Hz, 1H), 4.75-4.69 (m, 1H), 3.71 (s, 2H), 2.99 (dd, J=10.0, 6.4 Hz, 1H), 2.89 (s, 4H), 2.69 (dd, J=10.0, 3.7 Hz, 1H), 2.62 (td, J=8.7, 6.0 Hz, 1H), 2.45 (m, J=13.8, 8.2, 5.8 Hz, 1H), 1.84 (m, J=13.6, 8.1, 6.0, 3.7 Hz, 1H); $^{13}$C NMR (101 MHz, Methanol-$d_4$) δ 171.1, 150.0, 149.2, 143.6, 136.9, 133.1, 130.5, 128.6, 121.6, 105.8, 103.9, 102.4, 61.9, 59.6, 53.0, 52.9, 49.6, 49.4, 49.2, 49.0, 48.8, 48.6, 48.4, 34.0, 26.4; HRMS (ESI, m/z) calculated for $C_{20}H_{23}ClN_5O$ [M+H]$^+$ 384.1586 found 384.1588.

4-((1-(3-Methoxybenzyl)pyrrolidin-3-yl)amino)-N-methyl-1H-pyrrolo[2,3-b]pyridine-5-carboxamide 15d The title compound was synthesized according to General procedure D. Yield: 33.6%; $^1$H NMR (400 MHz, Methanol-$d_4$) δ 8.18 (s, 1H), 7.25-7.19 (m, 1H), 7.10 (d, J=3.6 Hz, 1H), 6.97 (dd, J=2.6, 1.4 Hz, 1H), 6.95-6.92 (m, 1H), 6.81 (m, J=8.2, 2.6, 1.0 Hz, 1H), 6.65 (d, J=3.7 Hz, 1H), 4.73 (m, J=10.3, 7.8, 3.9 Hz, 1H), 3.78 (s, 3H), 3.75-3.65 (m, 2H), 3.01 (dd, J=10.1, 6.4 Hz, 1H), 2.88 (s, 4H), 2.67 (m, J=18.8, 9.4, 5.0 Hz, 2H), 2.51-2.41 (m, 1H), 1.89-1.81 (m, 1H); $^{13}$C NMR (101 MHz, Methanol-$d_4$) δ 171.0, 159.8, 150.0, 149.1, 143.4, 139.6, 129.5, 121.6, 121.5, 114.4, 113.1, 105.7, 103.9, 102.4, 61.8, 60.3, 55.3, 52.9, 33.9, 26.4; HRMS (ESI, m/z) calculated for $C_{21}H_{26}N_5O_2$ [M+H]$^+$ 380.2081 found 380.2076.

4-((1-(4-Methoxybenzyl)pyrrolidin-3-yl)amino)-N-methyl-1H-pyrrolo[2,3-b]pyridine-5-carboxamide 15e The title compound was synthesized according to General procedure D. Yield: 18.6%; $^1$H NMR (400 MHz, Methanol-$d_4$) δ 8.19 (s, 1H), 7.33-7.26 (m, 2H), 7.11 (d, J=3.7 Hz, 1H), 6.91-6.86 (m, 2H), 6.64 (d, J=3.7 Hz, 1H), 4.76 (m, J=10.8, 8.0, 4.1 Hz, 1H), 3.78 (s, 3H), 3.74 (s, 2H), 3.12 (dd, J=10.4, 6.5 Hz, 1H), 2.96-2.89 (m, 1H), 2.88 (s, 3H), 2.79-2.71 (m; 2H), 2.53-2.43 (m, 1H), 1.92-1.81 (m, 1H); $^{13}$C NMR (101 MHz, Methanol-$d_4$) δ 171.4, 159.5, 150.1, 149.4, 143.8, 130.8, 122.0, 114.2, 106.0, 104.2, 102.4, 61.6, 59.8, 55.5, 53.0, 52.9, 33.9, 26.5; HRMS (ESI, m/z) calculated for $C_{21}H_{26}N_5O_2$ [M+H]$^+$ 380.2081 found 380.2079.

(R)-4-((1-(3-chlorobenzyl)pyrrolidin-3-yl)amino)-N-methyl-1H-pyrrolo[2,3-b]pyridine-5-carboxamide 15f The title compound was synthesized according to General procedure D. Yield: 38.4%; $^1$H NMR (400 MHz, Methanol-$d_4$) δ 8.18 (s, 1H), 7.42 (m, J=1.4, 0.9 Hz, 1H), 7.31-7.29 (m, 2H), 7.28-7.23 (m, 1H), 7.10 (d, J=3.7 Hz, 1H), 6.65 (d, J=3.7 Hz, 1H), 4.72 (m, J=10.2, 7.6, 3.8 Hz, 1H), 3.69 (s, 2H), 2.97 (dd, J=9.9, 6.4 Hz, 1H), 2.87-2.81 (m, 1H), 2.67 (dd, J=9.9, 3.7 Hz, 1H), 2.59 (m, J=8.7, 6.0 Hz, 1H), 2.45 (m, J=13.8, 8.2, 5.8 Hz, 1H), 1.88-1.79 (m, 1H). $^{13}$C NMR (101 MHz, Methanol-$d_4$) δ 171.3, 150.1, 149.3, 143.7, 140.7, 134.5, 130.0, 129.2, 127.7, 127.3, 121.8, 105.9, 104.1, 102.5, 62.0, 59.9, 53.0, 34.1, 26.5; HRMS (ESI, m/z) calculated for $C_{20}H_{23}ClN_5O$ [M+H]$^+$ 384.1586 found 384.1590.

(R)-4-((1-(4-Chlorobenzyl)pyrrolidin-3-yl)amino)-N-methyl-1H-pyrrolo[2,3-b]pyridine-5-carboxamide 15g The title compound was synthesized according to General procedure D. Yield: 57.6%; $^1$H NMR (400 MHz, Chloroform-d) δ 9.42 (s, 1H), 9.31 (d, J=7.5 Hz, 1H), 8.21 (s, 1H), 7.32-7.26 (m, 4H), 7.02 (d, J=3.6 Hz, 1H), 6.59 (d, J=3.7 Hz, 1H), 6.16 (s, 1H), 4.64 (m, J=11.4, 3.9 Hz, 1H), 3.64 (d, J=1.0 Hz, 2H), 3.04-2.97 (m, 4H), 2.80-2.72 (m, 1H), 2.61 (ddd, J=13.3, 9.2, 4.8 Hz, 2H), 2.45-2.35 (m, 1H), 1.92-1.84 (m, 1H); $^{13}$C NMR (101 MHz, Methanol-$d_4$) δ 171.5, 150.2, 149.6, 144.0, 137.1, 133.4, 130.7, 128.9, 122.0, 106.0, 104.2, 102.5, 62.1, 59.8, 53.3, 53.1, 34.2, 26.5; HRMS (ESI, m/z) calculated for $C_{20}H_{23}ClN_5O$ [M+H]$^+$ 384.1586 found 384.1590.

(S)-4-((1-(3-Chlorobenzyl)pyrrolidin-3-yl)amino)-N-methyl-1H-pyrrolo[2,3-b]pyridine-5-carboxamide 15h The title compound was synthesized according to General procedure D. Yield: 32.6%; $^1$H NMR (400 MHz, Methanol-$d_4$) δ 8.18 (s, 1H), 7.43-7.41 (m, 1H), 7.32-7.29 (m, 2H), 7.28-7.23 (m, 1H), 7.10 (d, J=3.7 Hz, 1H), 6.65 (d, J=3.7 Hz, 1H), 4.72 (m, J=10.2, 7.8, 3.9 Hz, 1H), 3.69 (s, 2H), 2.97 (dd, J=9.9, 6.3 Hz, 1H), 2.89 (s, 3H), 2.88-2.82 (m, 1H), 2.68 (dd, J=9.9, 3.7 Hz, 1H), 2.60 (m, J=8.7, 6.1 Hz, 1H), 2.45 (m, J=13.7, 8.1, 5.7 Hz, 1H), 1.89-1.79 (m, 1H); $^{13}$C NMR (101 MHz, Methanol-$d_4$) δ 170.5, 149.7, 148.8, 143.0, 140.4, 134.0, 129.5, 128.6, 127.1, 126.8, 121.2, 105.4, 103.6, 102.2, 61.6, 59.4, 52.7, 52.6, 33.7, 26.2; HRMS (ESI, m/z) calculated for $C_{20}H_{23}ClN_5O$ [M+H]$^+$ 384.1586 found 384.1590.

(S)-4-((1-(4-Chlorobenzyl)pyrrolidin-3-yl)amino)-N-methyl-1H-pyrrolo[2,3-b]pyridine-5-carboxamide 15i The title compound was synthesized according to General procedure D. Yield: 22.1%; $^1$H NMR (400 MHz, Chloroform-d) δ 9.72 (s, 1H), 9.30 (d, J=7.5 Hz, 1H), 8.22 (s, 1H), 7.32-7.26 (m, 4H), 7.02 (d, J=3.7 Hz, 1H), 6.58 (d, J=3.7 Hz, 1H), 6.18 (s, 1H), 4.64 (m, J=11.7, 7.7, 3.9 Hz, 1H), 3.64 (d, J=0.9 Hz, 2H), 3.00 (d, J=4.8 Hz, 4H), 2.76 (m, J=8.5, 6.8 Hz, 1H), 2.60 (m, J=14.4, 9.3, 4.9 Hz, 2H), 2.45-2.35 (m, 1H), 1.93-1.85 (m, 1H); $^{13}$C NMR (101 MHz, Methanol-$d_4$) 6'171.0, 150.0, 149.2, 143.5, 136.9, 133.0, 130.4, 128.6, 121.6, 105.7, 103.9, 102.3, 61.8, 59.5, 52.9, 52.8, 33.9, 26.4; FIRMS (ESI, m/z) calculated for $C_{20}H_{23}ClN_5O$ [M+H]$^+$ 384.1586 found 384.1590.

4-((3-(Benzylamino)cyclobutyl)amino)-N-methyl-1H-pyrrolo[2,3-b]pyridine-5-carboxamide 16a The title compound was synthesized according to General procedure D. Yield: 3.00%, $^1$H NMR (400 MHz, Methanol-$d_4$) trans (85%), δ 8.18 (s, 1H), 7.42-7.30 (m, 5H), 7.11 (d, J=3.7 Hz, 1H), 6.68 (d, J=3.7 Hz, 1H), 4.37 (m, J=8.4, 7.1 Hz, 1H), 3.87 (s, 2H), 3.37-3.28 (m, 1H), 2.94-2.85 (m, 1H), 2.87 (s, 3H), 2.01-1.90 (m, 2H); HRMS (ESI, m/z) calculated for $C_{20}H_{24}N_5O$ [M+H]$^+$ 350.1975 found 350.1979.

4-((3-((3-Chlorobenzyl)amino)cyclobutyl)amino)-N-methyl-1H-pyrrolo[2,3-b]pyridine-5-carboxamide 16b The title compound was synthesized according to General procedure D. Yield: 32.8%, $^1$H NMR (400 MHz, Methanol-$d_4$) δ 8.18 (d, J=6.7 Hz, 1H), 7.37-7.30 (m, 4H), 7.10 (d, J=3.7 Hz, 1H), 6.67 (d, J=3.7 Hz, 1H), 4.30 (tt, J=8.4, 7.0 Hz, 1H), 3.74 (s, 2H), 3.17 (tt, J=8.7, 7.1 Hz, 1H), 2.88 (s, 1H), 2.87 (s, 3H), 2.86-2.80 (m, 1H), 1.86 (tdd, J=11.7, 5.8, 2.7 Hz, 2H). HRMS (ESI, m/z) calculated for $C_{20}H_{23}ClN_5O$ [M+H]$^+$ 384.1586 found 384.1588.

4-((3-((4-Chlorobenzyl)amino)cyclobutyl)amino)-N-methyl-1H-pyrrolo[2,3-b]pyridine-5-carboxamide 16c The title compound was synthesized according to General procedure D. Yield: 13.6% (trans:cis=2.5), $^1$H NMR (400

MHz, Methanol-$d_4$) δ 8.2 (s, 1H), 8.2 (s, 2H), 7.4-7.2 (m, 18H), 7.1 (d, J=3.6 Hz, 2H), 7.1 (d, J=3.6 Hz, 1H), 6.7 (d, J=3.7 Hz, 2H), 6.6 (d, J=3.7 Hz, 1H), 4.7-4.6 (m, 1H), 4.4-4.2 (m, 2H), 3.7 (s, 5H), 3.7 (s, 2H), 3.6-3.5 (m, 1H), 3.2-3.1 (m, 3H), 2.9 (s, 3H), 2.9 (s, 7H), 2.9-2.8 (m, 5H), 2.6 (d, J=11.7 Hz, 1H), 2.4-2.4 (m, 2H), 2.3-2.2 (m, 3H), 1.8 (qd, J=8.7, 2.8 Hz, 5H). HRMS (ESI, m/z) calculated for $C_{20}H_{23}ClN_5O$ $[M+H]^+$ 384.1586 found 384.1589.

4-((3-((3-Chlorobenzyl)amino)cyclobutyl)amino)-1H-pyrrolo[2,3-b]pyridine-5-carboxamide 16d The title compound was synthesized according to General procedure D. Yield: 35.0%; $^1$H NMR (400 MHz, Methanol-$d_4$) δ 8.3 (s, 1H), 7.4 (d, J=1.9 Hz, 1H), 7.3-7.3 (m, 3H), 7.1 (d, J=3.7 Hz, 1H), 6.7 (d, J=3.7 Hz, 1H), 4.4-4.3 (m, 1H), 3.8 (s, 2H), 3.5 (p, J=6.5 Hz, 1H), 2.9-2.8 (m, 2H), 1.9 (qd, J=8.8, 2.9 Hz, 2H); HRMS (ESI, m/z) calculated for $C_{19}H_{20}ClN_5O$ $[M+H]^+$ 370.1439 found 370.1431.

4-((8-Benzyl-8-azabicyclo[3.2.1]octan-3-yl)amino)-N-methyl-1H-pyrrolo[2,3-b]pyridine-5-carboxamide 17a The title compound was synthesized according to General procedure D. Yield: 36.9%; $^1$H NMR (400 MHz, Methanol-$d_4$) δ 8.17 (s, 1H), 7.46-7.41 (m, 2H), 7.35 (tt, J=6.5, 1.0 Hz, 2H), 7.32-7.25 (m, 1H), 7.15 (d, J=3.6 Hz, 1H), 6.64 (d, J=3.7 Hz, 1H), 4.42 (m, J=11.4, 5.8 Hz, 1H), 3.73 (s, 2H), 3.42 (s, 2H), 2.87 (s, 3H), 2.29-2.21 (m, 2H), 2.15-2.08 (m, 2H), 1.92 (t, J=7.2 Hz, 2H), 1.77 (t, J=11.7 Hz, 2H); $^{13}$C NMR (101 MHz, Methanol-$d_4$) δ 170.8, 150.0, 149.1, 143.4, 139.1, 128.8, 128.4, 127.1, 121.4, 105.2, 103.9, 102.5, 58.6, 55.4, 45.5, 38.4, 26.9, 26.4; HRMS (ESI, m/z) calculated for $C_{23}H_{28}N_5O$ $[M+H]^+$ 390.2288 found 390.2293.

4-((8-(3-Chlorobenzyl)-8-azabicyclo[3.2.1]octan-3-yl)amino)-N-methyl-1H-pyrrolo[2,3-b]pyridine-5-carboxamide 17b The title compound was synthesized according to General procedure D. Yield: 51.8%; $^1$H NMR (400 MHz, Methanol-$d_4$) δ 8.16 (s, 1H), 7.49 (dt, J=2.0, 1.0 Hz, 1H), 7.37-7.25 (m, 3H), 7.14 (d, J=3.6 Hz, 1H), 6.65 (d, J=3.7 Hz, 1H), 4.39 (tt, J=11.3, 5.7 Hz, 1H), 3.66 (s, 2H), 3.37-3.32 (m, 2H), 2.87 (s, 3H), 2.25-2.18 (m, 2H), 2.13-2.05 (m, 2H), 1.89 (t, J=7.2 Hz, 2H), 1.75 (t, J=12.0 Hz, 2H); $^{13}$C NMR (101 MHz, Methanol-$d_4$) δ 171.7, 150.3, 149.7, 144.2, 141.7, 134.6, 130.0, 129.2, 127.6, 127.4, 122.0, 105.7, 104:3, 102.6, 59.1, 55.4, 45.7, 38.9, 27.1, 26.5; HRMS (ESI, m/z) calculated for $C_{23}H_{27}ClN_5O$ $[M+H]^+$ 424.1899 found 424.1903.

4-((8-(4-Chlorobenzyl)-8-azabicyclo[3.2.1]octan-3-yl)amino)-N-methyl-1H-pyrrolo[2,3-b]pyridine-5-carboxamide 17c The title compound was synthesized according to General procedure D. Yield: 38.7%; $^1$H NMR (400 MHz, Methanol-$d_4$) δ 8.17 (s, 1H), 7.46-7.35 (m, 4H), 7.15 (d, J=3.6 Hz, 1H), 6.65 (d, J=3.7 Hz, 1H), 4.42 (m, J=11.2, 5.8 Hz, 1H), 3.73 (s, 2H), 3.43 (s, 2H), 2.86 (s, 3H), 2.29-2.22 (m, 2H), 2.17-2.11 (m, 2H), 1.94 (d, J=7.8 Hz, 2H), 1.76 (t, J=12.1 Hz, 2H); $^{13}$C NMR (101 MHz, Methanol-$d_4$) δ 171.6, 150.3, 149.6, 144.0, 137.5, 133.4, 130.7, 128.9, 122.1, 105.7, 104.3, 102.6, 59.1, 55.0, 45.7, 38.7, 27.0, 26.5; HRMS (ESI, m/z) calculated for $C_{23}H_{27}ClN_5O$ $[M+H]^+$ 424.1899 found 424.1903.

General Procedure E

4 N HCl in dioxane (2 mL) was added to a solution of compound 9-13 in MeOH. The mixture was stirred at room temperature for 1 h to remove the Boc group on the amine. The product was dried under vacuum and used without further purification. Triethylamine (2 eq) and sodium triacetoxyborohydride (2 eq) were added to an appropriate solution of the Boc deprotected intermediate (0.25 mmol) and benzaldehyde (0.5 mmol) in DCM (5 ml), followed by stirring at room temperature for 24 h. The resulting mixture was washed with a saturated aqueous solution of $NaHCO_3$, diluted with ethyl acetate, washed with $H_2O$ and brine, and dried over $MgSO_4$. The crude mixture was purified by silica gel flash chromatography (dichloromethane:MeOH=10:1 elution) to afford a title product.

4-((8-(3-Methoxybenzyl)-8-azabicyclo[3.2.1]octan-3-yl)amino)-N-methyl-1H-pyrrolo[2,3-b]pyridine-5-carboxamide 17d The title compound was synthesized according to General procedure E. Yield: 59.4% (endo:exo=1:1); $^1$H NMR (400 MHz, Chloroform-d) δ 9.6 (d, J=7.4 Hz, 1H), 9.4 (s, 1H), 9.3 (s, 1H), 9.0 (d, J=8.1 Hz, 1H), 8.2 (s, 1H), 8.2 (s, 1H), 7.3-7.2 (m, 2H), 7.1-6.9 (m, 6H), 6.8 (d, J=2.5 Hz, 1H), 6.8 (s, 1H), 6.6 (d, J=3.7 Hz, 1H), 6.5 (d, J=3.6 Hz, 1H), 6.0 (s, 2H), 4.3 (q, J=6.4 Hz, 2H), 3.8 (s, 3H), 3.8 (s, 3H), 3.6 (s, 2H), 3.6 (s, 2H), 3.3 (s, 2H), 3.2 (s, 2H), 3.0 (t, J=5.0 Hz, 6H), 2.3 (dd, J=8.0, 4.0 Hz, 2H), 2.1 (s, 4H), 2.1-2.0 (m, 2H), 1.9-1.7 (m, 8H); HRMS (ESI, m/z) calculated for $C_{24}H_{29}N_5O_2$ $[M+H]^+$ 420.2394 found 420.2395.

4-((8-(4-Methoxybenzyl)-8-azabicyclo[3.2.1]octan-3-yl)amino)-N-methyl-1H-pyrrolo[2,3-b]pyridine-5-carboxamide 17e The title compound was synthesized according to General procedure E. Yield: 70.7% (endo:exo=1:1); $^1$H NMR (400 MHz, Chloroform-d) δ 9.6 (d, J=7.4 Hz, 1H), 9.6 (s, 1H), 9.5 (s, 1H), 9.0 (d, J=8.4 Hz, 1H), 8.2 (d, J=4.5 Hz, 2H), 7.3 (d, J=8.6 Hz, 4H), 7.1 (d, J=3.6 Hz, 1H), 7.0 (d, J=3.5 Hz, 1H), 6.9 (dd, J=8.6, 1.9 Hz, 4H), 6.6 (d, J=3.7 Hz, 1H), 6.5 (d, J=3.6 Hz, 1H), 6.0 (s, 1H), 4.3 (d, J=6.8 Hz, 2H), 3.8 (s, 6H), 3.6 (s, 2H), 3.5 (s, 2H), 3.3 (s, 2H), 3.2 (s, 2H), 3.0 (dd, J=6.5, 4.5 Hz, 6H), 2.3 (ddd, J=14.2, 6.3, 3.6 Hz, 2H), 2.1 (d, J=12.0 Hz, 6H), 2.0 (dd, J=7.9, 3.6 Hz, 2H), 1.9 (d, J=13.7 Hz, 2H), 1.9-1.7 (m, 6H).

4-((8-(3-Cyanobenzyl)-8-azabicyclo[3.2.1]octan-3-yl)amino)-N-methyl-1H-pyrrolo[2,3-b]pyridine-5-carboxamide 17f The title compound was synthesized according to General procedure E. Yield: 54.5% (endo:exo=1:1); $^1$H NMR (400 MHz, Chloroform-d) δ 9.7 (d, J=7.2 Hz, 1H), 9.1 (d, J=8.6 Hz, 1H), 8.3 (s, 1H), 8.2 (s, 1H), 8.2 (d, J=3.8 Hz, 2H), 8.2-8.0 (m, 2H), 7.8 (d, J=7.6 Hz, 1H), 7.7 (d, J=7.4 Hz, 1H), 7.5 (td, J=7.9, 5.5 Hz, 2H), 7.1 (d, J=3.7 Hz, 1H), 7.0 (d, J=3.7 Hz, 1H), 6.6 (d, J=3.7 Hz, 1H), 6.5 (d, J=3.7 Hz, 1H), 6.1 (s, 2H), 4.4 (q, J=6.8 Hz, 2H), 3.7 (s, 2H), 3.7 (s, 2H), 3.3 (s, 2H), 3.2 (s, 2H), 3.1-2.9 (m, 6H), 2.4-2.3 (m, 2H), 2.2-2.1 (m, 6H), 2.1-2.0 (m, 2H), 1.9 (d, J=13.8 Hz, 2H), 1.9-1.8 (m, 4H); HRMS (ESI, m/z) calculated for $C_{24}H_{26}N_6O$ $[M+H]^+$ 415.2241 found 415.2245.

4-((8-(4-Cyanobenzyl)-8-azabicyclo[3.2.1]octan-3-yl)amino)-N-methyl-1H-pyrrolo[2,3-b]pyridine-5-carboxamide 17r The title compound was synthesized according to General procedure E. Yield: 67.6% (endo:exo=1:1); $^1H$ NMR (400 MHz, Chloroform-d) δ 9.7 (d, J=7.5 Hz, 1H), 9.1 (d, J=7.9 Hz, 11H), 8.2 (s, 11H), 8.2 (s, 11H), 7.6 (d, J=8.1 Hz, 4H), 7.5 (d, J=7.2 Hz, 4H), 7.0 (d, J=3.6 Hz, 1H), 7.0-7.0 (m, 1H), 6.6 (d, J=3.5 Hz, 1H), 6.5 (d, J=3.5 Hz, 1H), 6.2 (s, 2H), 4.3 (q, J=6.5 Hz, 2H), 3.7 (s, 2H), 3.6 (s, 2H), 3.2 (s, 2H), 3.2 (s, 2H), 3.0 (dd, J=4.8, 3.3 Hz, 5H), 2.4-2.3 (m, 2H), 2.2-2.1 (m, 7H), 2.1 (dd, J=7.9, 3.3 Hz, 2H), 1.9 (d, J=13.4 Hz, 2H), 1.8 (dd, J=15.6, 9.4 Hz, 5H).

(S)-4-((1-(3-Chlorobenzyl)piperidin-3-yl)amino)-N-methyl-1H-pyrrolo[2,3-b]pyridine-5-carboxamide 18a The title compound was synthesized according to General procedure E. Yield: 43.3%; $^1H$ NMR (400 MHz, Chloroform-d) δ 9.29 (s, 2H), 8.17 (s, 1H), 7.50 (s, 1H), 7.23 (d, J=0.7 Hz, 1H), 7.22-7.17 (m, 2H), 7.00 (d, J=3.7 Hz, 1H), 6.51 (d, J=3.7 Hz, 1H), 6.03 (s, 1H), 4.16 (d, J=9.3 Hz, 1H), 3.58-3.44 (m, 2H), 3.01 (d, J=4.8 Hz, 3H), 2.97-2.87 (m, 1H), 2.66-2.55 (m, 1H), 2.41-2.31 (m, JH), 2.24 (s, 1H), 1.98 (d, J=6.0 Hz, 1H), 1.90-1.83 (m, 1H), 1.66 (s, 2H); HRMS (ESI, m/z) calculated for $C_{22}H_{27}N_5O_2$ $[M+H]^+$ 394.2238 found 394.2235.

(S)-4-((1-(3-Methoxybenzyl)piperidin-3-yl)amino)-N-methyl-1H-pyrrolo[2,3-b]pyridine-5-carboxamide 18b The title compound was synthesized according to General procedure E. Yield: 69.2%; $^1H$ NMR (400 MHz, Chloroform-d) δ 9.26 (d, J=7.9 Hz, 2H), 8.17 (s, 1H), 7.20 (dd, J=8.2, 7.5 Hz, 1H), 7.03 (s, 1H), 6.99-6.94 (m, 2H), 6.81-6.74 (m, 1H), 6.54 (d, J=3.7 Hz, 1H), 6.07 (s, 1H), 4.21-4.12 (m, 1H), 3.83 (s, 3H), 3.58-3.47 (m, 2H), 2.99 (d, J=4.8 Hz, 3H), 2.97 (s, 1H), 2.60 (s, 1H), 2.39-2.31 (m, 1H), 2.27 (s, 1H), 1.98 (s, 1H), 1.85 (dd, J=6.3, 3.5 Hz, 1H), 1.64 (s, 2H); HRMS (ESI, m/z) calculated for $C_{21}H_{25}ClN_5O$ $[M+H]^+$ 398.1742 found 398.1747.

4-((1-Benzylazepan-4-yl)amino)-N-methyl-1H-pyrrolo[2,3-b]pyridine-5-carboxamide 19a The title compound was synthesized according to General procedure E. Yield: 76.3%; $^1H$ NMR (400 MHz, Methanol-$d_4$) δ 8.17 (s, 1H), 7.43-7.27 (m, 5H), 7.09 (d, J=3.7 Hz, 1H), 6.62 (d, J=3.7 Hz, 1H), 4.44-4.36 (m, 1H), 3.86-3.75 (m, 2H), 2.87 (s, 7H), 2.26-2.16 (m, 2H), 1.95-1.75 (m, 4H); $^{13}C$ NMR (101 MHz, Methanol-$d_4$) δ 163.2, 141.3, 141.1, 135.6, 121.3, 121.0, 120.7, 120.1, 119.4, 118.6, 113.4, 97.2, 95.5, 93.8, 53.9, 46.9, 44.0, 41.9, 26.3, 25.3, 17.2, 14.6; HRMS (ESI, m/z) calculated for $C_{22}H_{28}N_5O$ $[M+H]^+$ 378.2288 found 378.2292.

4-((1-(3-Chlorobenzyl)azepan-4-yl)amino)-N-methyl-1H-pyrrolo[2,3-b]pyridine-5-carboxamide 19b The title compound was synthesized according to General procedure E. Yield: 55.9%; $^1H$ NMR (400 MHz, Methanol-$d_4$) δ 8.17 (s, 1H), 7.44 (m, J=1.4, 0.8 Hz, 1H), 7.34-7.23 (m, 3H), 7.09 (d, J=3.7 Hz, 1H), 6.62 (d, J=3.7 Hz, 1H), 4.41 (m, J=8.2, 4.2 Hz, 1H), 3.72-3.62 (m, 2H), 2.88 (s, 3H), 2.84-2.67 (m, 4H), 2.17 (m, J=12.6, 9.4, 8.0, 4.2 Hz, 2H), 1.92-1.69 (m, 4H); $^{13}C$ NMR (101 MHz, Methanol-$d_4$) δ 171.1, 149.7, 149.2, 143.6, 141.4, 134.2, 129.6, 129.0, 127.3, 127.2, 121.3, 105.4, 103.7, 102.7, 62.5, 55.8, 52.7, 50.9, 35.3, 34.8, 26.4, 24.5. HRMS (ESI, m/z) calculated for $C_{22}H_{27}ClN_5O$ $[M+H]^+$ 412.1899 found 412.1903.

4-((1-(4-Chlorobenzyl)azepan-4-yl)amino)-N-methyl-1H-pyrrolo[2,3-b]pyridine-5-carboxamide 19c The title compound was synthesized according to General procedure E. Yield: 58.4%; $^1H$ NMR (400 MHz, Methanol-$d_4$) δ 8.17 (s, 1H), 7.40-7.32 (m, 4H), 7.09 (d, J=3.6 Hz, 1H), 6.61 (d, J=3.7 Hz, 1H), 4.40 (m, J=8.1, 4.2 Hz, 1H), 3.69 (d, J=2.2 Hz, 2H), 2.88 (s, 3H); 2.85-2.69 (m, 4H), 2.24-2.13 (m, 3H), 1.95-1.70 (m, 3H); $^{13}C$ NMR (101 MHz, Methanol-$d_4$) δ 171.3, 149.9, 149.2, 143.7, 137.4, 133.1, 130.7, 128.7, 121.6, 105.7, 103.9, 102.8, 62.3, 55.9, 52.9, 50.8, 35.1, 34.9, 26.5, 24.3. HRMS (ESI, m/z) calculated for $C_{22}H_{27}ClN_5O$ $[M+H]^+$ 412.1899 found 412.1904.

4-((1-(4-Methoxybenzyl)azepan-4-yl)amino)-N-methyl-1H-pyrrolo[2,3-b]pyridine-5-carboxamide 19d The title compound was synthesized according to General procedure E. Yield: 73.5%; $^1H$ NMR (400 MHz, Chloroform-d) δ 9.89 (s, 1H), 9.38 (d, J=8.0 Hz, 1H), 8.28 (s, 1H), 7.34 (d, J=8.4 Hz, 2H), 6.93 (d, J=3.5 Hz, 1H), 6.90-6.86 (m, 2H), 6.46 (d, J=3.7 Hz, 1H), 4.30 (s, 1H), 3.81 (s, 3H), 3.74 (s, 2H), 3.00 (d, J=4.7 Hz, 3H), 2.88 (d, J=0.6 Hz, 1H), 2.84 (s, 2H), 2.80-2.69 (m, 2H), 2.32-2.16 (m, 2H), 1.99-1.85 (m, 2H), 1.85-1.76 (m, 2H); $^{13}C$ NMR (101 MHz, Methanol-$d_4$) δ 170.6, 159.3, 149.6, 149.4, 148.5, 142.8, 131.0, 121.4, 113.9, 105:3, 103.5, 102.4, 61.5, 55.1, 55.0, 51.9, 34.4, 32.9, 26.4, 26.2, 22.6; FIRMS (ESI, m/z) calculated for $C_{23}H_{30}N_5O_2$ $[M+H]^+$ 408.23941 found 408.2390.

4-((1-(4-Cyanobenzyl)azepan-4-yl)amino)-N-methyl-1H-pyrrolo[2,3-b]pyridine-5-carboxamide 19e The title compound was synthesized according to General procedure E. Yield: 65.0%; $^1H$ NMR (400 MHz, Chloroform-d) δ 10.10 (s, 1H), 9.32 (d, J=8.1 Hz, 1H), 8.24 (s, 1H), 7.64-7.59 (m, 2H), 7.53-7.49 (m, 2H), 7.00 (d, J=3.6 Hz, 1H), 6.54 (d, J=3.7 Hz, 1H), 6.34 (s, 1H), 4.38-4.28 (m, 1H), 3.71 (s, 2H), 2.99 (d, J=4.7 Hz, 3H), 2.79-2.61 (m, 4H), 2.21-2.09 (m, 3H), 1.95-1.82 (m, 3H), 1.76-1.64 (m, 1H); $^{13}C$ NMR (101 MHz, Methanol-$d_4$) δ 170.7, 149.6, 148.6, 145.4, 143.0, 132.1, 129.3, 121.1, 118.9, 110.4, 105.3, 103.5, 102.5, 62.5, 55.7, 52.6, 51.0, 35.4, 34.3, 26.3, 24.5; HRMS (ESI, m/z) calculated for $C_{23}H_{27}N_6O$ $[M+H]^+$ 403.2241 found 403.2246.

4-((trans-1-Benzyl-2-methylpiperidin-4-yl)amino)-N-methyl-1H-pyrrolo[2,3-b]pyridine-5-carboxamide 20a The title compound was synthesized according to General procedure E. Yield: 49.3%; $^1H$ NMR (400 MHz, Chloroform-d) δ 9.97 (s, 1H), 9.47 (d, J=7.8 Hz, 1H), 8.24 (s, 1H), 7.41-7.29 (m, 4H), 7.25-7.23 (m, 1H), 7.00 (d, J=3.6 Hz, 1H), 6.54-6.50 (m, 1H), 6.41 (s, 1H), 4.33 (s, 1H), 4.02 (d, J=13.3 Hz, 1H), 3.35 (d, J=13.3 Hz, 1H), 3.01 (d, J=4.7 Hz, 3H), 2.96-2.88 (m, 1H), 2.73-2.67 (m, 1H), 2.50-2.42 (m, 1H), 1.94 (d, J=5.7 Hz, 3H), 1.84-1.75 (m, 1H), 1.23 (d, J=6.3 Hz, 3H); $^{13}$C NMR (101 MHz, Methanol-$d_4$) δ 171.8, 150.2, 149.7, 144.2, 137.2, 130.2, 128.9, 128.1, 122.1, 106.0, 104.1, 102.9, 58.7, 53.4, 46.7, 39.1, 31.1, 26.6, 17.8; HRMS (ESI, m/z) calculated for $C_{22}H_{28}N_5O$ $[M+H]^+$ 378.2288 found 378.2295.

4-((trans-1-(3-Chlorobenzyl)-2-methylpiperidin-4-yl)amino)-N-methyl-11H-pyrrolo[2,3-b]pyridine-5-carboxamide 20b The title compound was synthesized according to General procedure E. Yield: 45.4%; $^1$H NMR (400 MHz, Chloroform-d) δ 9.42 (d, J=7.8 Hz, 2H), 8.22 (s, 1H), 7.38 (d, J=2.1 Hz, 1H), 7.24-7.18 (m, 3H), 7.03 (d, J=3.6 Hz, 1H), 6.55 (d, J=3.7 Hz, 1H), 6.22 (s, 1H), 4.34 (s, 1H), 3.94 (d, J=13.7 Hz, 1H), 3.31 (d, J=13.8 Hz, 1H), 3.01 (d, J=4.8 Hz, 3H), 2.92-2.85 (m, 1H), 2.71-2.63 (m, 1H), 2.48-2.40 (m, 1H), 1.87-1.77 (m, 4H), 1.19 (d, J=6.3 Hz, 3H); $^{13}$C NMR (101 MHz, Methanol-$d_4$) δ 172.2, 150.5, 150.0, 144.5, 141.3, 135.0, 130.4, 130.1, 128.3, 128.1, 122.4, 106.3, 104.4, 103.3, 58.7, 53.3, 47.3, 47.1, 39.9, 32.0, 26.9, 18.0; HRMS (ESI, m/z) calculated for $C_{22}H_{27}ClN_5O$ $[M+H]^+$ 412.1899 found 412.1903.

4-((trans-1-(4-Chlorobenzyl-2-methylpiperidin-4-v)amino)-N-methyl-1H-pyrrolo[2,3-b]pyridine-5-carboxamide 20c The title compound was synthesized according to General procedure E. Yield: 57.3%; $^1$H NMR (400 MHz, Chloroform-d) δ 9.80 (s, 1H), 9.44 (d, J=7.8 Hz, 1H), 8.22 (s, 1H), 7.32-7.27 (m, 4H), 7.03 (d, J=3.6 Hz, 1H), 6.54 (d, J=3.7 Hz, 1H), 6.25 (s, 1H), 4.33 (s, 1H), 3.94 (d, J=13.6 Hz, 1H), 3.31 (d, J=13.6 Hz, 1H), 3.00 (d, J=4.7 Hz, 3H), 2.92-2.84 (m, 1H), 2.69-2.62 (m, 1H), 2.46-2.38 (m, 1H), 1.95 (dd, J=12.6, 3.9 Hz, 3H), 1.80 (d, J=11.2 Hz, 1H), 1.19 (d, J=6.3 Hz, 3H); $^{13}$C NMR (101 MHz, Methanol-$d_4$) δ 171.5, 150.1, 149.4, 143.9, 136.8, 133.3, 131.2, 128.8, 121.9, 105.8, 103.9, 102.9, 57.9, 52.8, 46.8, 39.3, 31.4, 26.6, 17.6; HRMS (ESI, m/z) calculated for $C_{22}H_{27}ClN_5O$ $[M+H]^+$ 412.1899 found 412.1903.

4-((trans-1-(3-Methoxybenzyl)-2-methylpiperidin-4-yl)amino)-N-methyl-1H-pyrrolo[2,3-b]pyridine-5-carboxamide 20d The title compound was synthesized according to General procedure E. Yield: 55.6%; $^1$H NMR (400 MHz, Chloroform-d) δ 9.98 (s, 1H), 9.47 (d, J=7.8 Hz, 1H), 8.23 (s, 1H), 7.23 (t, J=7.8 Hz, 1H), 7.01 (d, J=3.7 Hz, 1H), 6.99-6.92 (m, 2H), 6.81-6.77 (m, 1H), 6.53 (d, J=3.7 Hz, 1H), 6.34 (s, 1H), 4.33 (s, 1H), 3.99 (d, J=13.5 Hz, 1H), 3.82 (s, 3H), 3.35 (d, J=13.4 Hz, 1H), 3.00 (d, J=4.7 Hz, 3H), 2.97-2.91 (m, 1H), 2.76-2.69 (m, 1H), 2.52-2.44 (m, 1H), 2.05-2.00 (m, 1H), 1.95 (t, J=5.3 Hz, 2H), 1.84-1.75 (m, 1H), 1.22 (d, J=6.4 Hz, 3H); $^{13}$C NMR (101 MHz, Methanol-$d_4$) δ 171.6, 160.1, 150.1, 149.4, 143.9, 138.9, 129.7, 122.4, 121.9, 115.4, 113.5, 105.9, 104.0, 102.9, 58.6, 55.5, 53.3, 46.6, 39.0, 31.1, 26.6, 17.6; HRMS (ESI, m/z) calculated for $C_{23}H_{30}N_5O_2$ $[M+H]^+$ 408.2394 found 408.2399.

4-((trans-1-(4-Methoxybenzyl)-2-methylpiperidin-4-yl)amino)-N-methyl-1H-pyrrolo[2,3-b]pyridine-5-carboxamide 20e The title compound was synthesized according to General procedure E. Yield: 48.5%; $^1$H NMR (400 MHz, Chloroform-d) δ 10.20 (s, 1H), 9.54 (d, J=7.8 Hz, 1H), 8.23 (s, 1H), 7.31 (d, J=8.4 Hz, 2H), 7.01 (d, J=3.6 Hz, 1H), 6.89-6.85 (m, 2H), 6.50 (d, J=3.7 Hz, 2H), 4.34 (s, 1H), 4.05 (d, J=13.1 Hz, 1H), 3.81 (s, 3H), 3.36 (d, J=13.1 Hz, 1H), 3.02-2.95 (m, 4H), 2.77 (d, J=12.3 Hz, 1H), 2.49 (t, J=10.9 Hz, 1H), 2.00 (dd, J=28.9, 10.6 Hz, 3H), 1.83 (d, J=13.3 Hz, 1H), 1.29 (d, J=6.3 Hz, 3H); $^{13}$C NMR (101 MHz, Methanol-$d_4$) δ 171.5, 159.9, 150.0, 149.4, 143.8, 131.8, 127.1, 122.2, 114.4, 105.9, 104.0, 102.7, 57.6, 55.5, 53.7; 49.9, 46.3, 38.5, 30.3, 26.6, 17.6; HRMS (ESI, m/z) calculated for $C_{23}H_{30}N_5O_2$ $[M+H]^+$ 408.2394 found 408.2401.

4-((cis-1-(3-Chlorobenzyl)-2-methylpiperidin-4-yl)amino)-N-methyl-1H-pyrrolo[2,3-b]pyridine-5-carboxamide 20f The title compound was synthesized according to General procedure E. Yield: 65.1%; $^1$H NMR (400 MHz, Chloroform-d) δ 9.50 (s, 1H), 9.10-9.04 (m, 1H), 8.18 (s, 1H), 7.33 (d, J=2.0 Hz, 1H), 7.20 (tt, J=5.3, 3.4 Hz, 2H), 7.02 (d, J=3.7 Hz, 1H), 6.52 (d, J=3.7 Hz, 1H), 6.05 (s, 1H), 4.08 (d, 1=13.7 Hz, 1H), 3.98-3.87 (m, 1H), 3.11 (d, J=13.8 Hz, 1H), 2.96 (d, J=4.8 Hz, 3H), 2.91-2.83 (m, 1H), 2.48-2.37 (m, 1H), 2.19-2.11 (m, 1H), 2.10-2.02 (m, 2H), 1.50 (dt, J=12.7, 11.3 Hz, 2H), 1.21 (d, J=6.1 Hz, 2H); $^{13}$C NMR (101 MHz, Methanol-$d_4$) δ 170.9, 149.8, 149.3, 143.6, 140.9, 134.2, 129.5, 129.1, 127.3, 127.2, 121.3, 105.2, 103.6, 102.6, 57.7, 57.7, 57.1, 56.0, 51.5, 51.0, 42.0, 33.2, 26.3, 20.9; HRMS (ESI, m/z) calculated for $C_{22}H_{26}ClN_5O$ $[M+H]^+$ 412.1899 found 412.1904.

4-((cis-1-(4-Chlorobenzyl)-2-methylpiperidin-4-yl)amino)-N-methyl-1H-pyrrolo[2,3-b]pyridine-5-carboxamide 20g The title compound was synthesized according to General procedure E. Yield: 62.6%; $^1$H NMR (400 MHz, Chloroform-d) δ 9.39 (s, 1H), 9.12-9.05 (m, 1H), 8.20 (s, 1H), 7.31-7.27 (m, 4H), 7.03 (d, J=3.7 Hz, 1H), 6.53 (d, J=3.7 Hz, 1H), 6.05 (s, 1H), 4.08 (d, J=13.7 Hz, 1H), 4.00-3.87 (m, 1H), 3.12 (d, J=13.7 Hz, 1H), 2.98 (d, J=4.8 Hz, 3H), 2.89-2.83 (m, 1H), 2.48-2.39 (m, 1H), 2.19-2.13 (m, 1H), 2.12-2.03 (m, 2H), 1.61-1.45 (m, 2H), 1.23 (d, J=6.1 Hz, 3H). $^{13}$C NMR (101 MHz, Methanol-$d_4$) δ 171.7, 150.1, 149.9, 144.3, 137.1, 133.3, 131.2, 128.8, 122.0, 105.8, 104.1, 102.8, 57.3, 56.5, 51.8, 51.4, 42.5, 33.7, 26.5, 21.1; HRMS (ESI, m/z) calculated for $C_{22}H_{26}ClN_5O$ $[M+H]^+$ 412.1903 found 412.1899.

4-((cis-1-(3-Methoxybenzyl)-2-methylpiperidin-4-yl)amino)-N-methyl-1H-pyrrolo[2,3-b]pyridine-5-carboxamide 20h The title compound was synthesized according to General procedure E. Yield: 66.2%; $^1$H NMR (400 MHz, Chloroform-d) δ 9.66 (s, 1H), 9.09 (d, J=7.9 Hz, 1H), 8.20 (s, 1H), 7.22 (d, J=8.0 Hz, 1H), 7.03 (d, J=3.6 Hz, 1H), 6.93-6.90 (m, 2H), 6.82-6.77 (m, 1H), 6.53 (d, J=3.7 Hz, 1H), 6.09 (s, 1H), 4.11 (d, J=13.5 Hz, 1H), 3.99-3.88 (m, 1H), 3.82 (s, 3H), 3.15 (d, J=13.6 Hz, 1H), 2.98 (d, J=4.8 Hz, 3H), 2.92 (dt, J=11.9, 3.4 Hz, 1H), 2.47-2.40 (m, 1H), 2.20-2.05 (m, 3H), 1.64-1.47 (m, 2H), 1.24 (d, J=6.1 Hz, 4H); $^{13}C$ NMR (101 MHz, Chloroform-d) δ 170.9, 158.7, 149.7, 149.3, 143.5, 130.7, 129.7, 121.2, 113.6, 105.2, 103.6, 102.6, 56.7, 55.7, 55.2, 51.0, 41.9, 33.1, 26.3, 20.8; HRMS (ESI, m/z) calculated for $C_{23}H_{29}N_5O_2$ $[M+H]^+$ 408.2394 found 408.2403.

4-((cis-1-(4-Methoxybenzyl)-2-methylpiperidin-4-yl)amino)-N-methyl-1H-pyrrolo[2,3-b]pyridine-5-carboxamide 20i The title compound was synthesized according to General procedure E. Yield: 90.5%; $^1H$ NMR (400 MHz, Chloroform-d) δ 9.66 (s, 1H), 9.07 (d, J=7.9 Hz, 1H), 8.20 (s, 1H), 7.26-7.22 (m, 2H), 7.03 (d, J=3.6 Hz, 1H), 6.88-6.84 (m, 2H), 6.52 (d, J=3.7 Hz, 1H), 6.06 (s, 1H), 4.06 (d, J=13.3 Hz, 1H), 3.97-3.86 (m, 1H), 3.81 (s, 3H), 3.15 (d, J=13.3 Hz, 1H), 2.97 (d, J=4.8 Hz, 3H), 2.94-2.87 (m, 1H), 2.45-2.36 (m, 1H), 2.15 (dd, J=12.9, 2.7 Hz, 1H), 2.11-2.02 (m, 2H), 1.63-1.46 (m, 2H), 1.26 (d, J=6.1 Hz, 3H); $^{13}C$ NMR (101 MHz, Chloroform-d) δ 170.9, 159.6, 149.7, 149.3, 143.5, 139.9, 129.2, 121.7, 121.2, 114.9, 112.4, 105.2, 103.6, 102.6, 57.5, 55.9, 55.2, 51.4, 51.0, 42.0, 33.2, 26.3, 20.9; HRMS (ESI, m/z) calculated for $C_{23}H_{29}N_5O_2$ $[M+H]^+$ 408.2394 found 408.2394.

4-((cis-1-(4-Cyanobenzyl)-2-methylpiperidin-4-yl)amino)-N-methyl-1H-pyrrolo[2,3-b]pyridine-5-carboxamide 20j The title compound was synthesized according to General procedure E. Yield: 91.4%; $^1H$ NMR (400 MHz, Chloroform-d) δ 9.67 (s, 1H), 9.12 (d, J=7.9 Hz, 1H), 8.21 (s, 1H), 7.63-7.44 (m, 4H), 7.04 (d, J=3.7 Hz, 1H), 6.53 (d, J=3.7 Hz, 1H), 6.09 (s, 1H), 4.16 (d, J=14.3 Hz, 1H), 4.01-3.91 (m, 1H), 3.19 (d, J=14.4 Hz, 1H), 2.98 (d, J=4.8 Hz, 3H), 2.82 (dt, J=12.4, 3.5 Hz, 1H), 2.51-2.42 (m, 1H), 2.22-2.04 (m, 3H), 1.49 (d, J=11.8 Hz, 2H), 1.20 (d, J=6.1 Hz, 3H); $^{13}C$ NMR (101 MHz, Chloroform-d) δ 170.8, 149.8, 149.3, 145.5, 143.5, 132.1, 129.4, 121.3, 119.0, 110.5, 105.2, 103.6, 102.5, 57.3, 56.2, 51.9, 51.0, 42.1, 33.3, 26.4, 21.1; HRMS (ESI, m/z) calculated for $C_{23}H_{26}N_6O$ $[M+H]^+$ 403.2241 found 403.2247.

4-((trans-1-(3-Chlorobenzyl)-3-fluoropiperidin-4-yl)amino)-N-methyl-1H-pyrrolo[2,3-b]pyridine-5-carboxamide 21a The title compound was synthesized according to General procedure E. Yield: 24.6%; $^1H$ NMR (400 MHz, Chloroform-d) δ 10.7 (s, 1H), 9.5 (d, J=8.0 Hz, 1H), 8.3 (s, 1H), 7.4 (s, 1H), 7.3-7.2 (m, 3H), 7.0 (d, J=3.5 Hz, 1H), 6.5 (d, J=3.5 Hz, 1H), 6.0 (s, 1H), 4.4-4.3 (m, 1H), 3.7-3.6 (m, 2H), 2.8-2.6 (m, 4H), 2.2-2.1 (m, 2H), 1.9 (ddt, J=23.9, 12.9, 5.9 Hz, 3H), 1.8-1.6 (m, 1H); HRMS (ESI, m/z) calculated for $C_{21}H_{23}ClFN_5O$ $[M+H]^+$ 416.1648 found 416.1648.

4-((cis-3-Fluoro-1-(3-methoxybenzyl)piperidin-4-yl)amino)-N-methyl-11H-pyrrolo[2,3-b]pyridine-5-carboxamide 21b The title compound was synthesized according to General procedure E. Yield: 39.6%; $^1H$ NMR (400 MHz, Chloroform-d) δ 9.90 (s, 1H), 9.51 (d, J=8.5 Hz, 1H), 8.21 (s, 1H), 7.23 (d, J=7.8 Hz, 1H), 7.06 (d, J=3.7 Hz, 1H), 6.96-6.90 (m, 2H), 6.84-6.79 (m, 1H), 6.46 (d, J=3.7 Hz, 1H), 6.10 (s, 1H), 4.87 (d, J=48.7 Hz, 1H), 4.18 (d, J=24.4 Hz, 1H), 3.82 (s, 3H), 3.62-3.60 (m, 2H), 3.21 (s, 1H), 3.00 (d, J=4.7 Hz, 3H), 2.96-2.87 (m, 1H), 2.52-2.28 (m, 2H), 2.18-2.06 (m, 2H); HRMS (ESI, m/z) calculated for $C_{22}H_{27}FN_5O_2[M+H]^+$ 412.2143 found 412.2145.

[General Scheme III]-Experimental procedure for synthesis of intermediates 2, 7″-10″ and 18″-20″

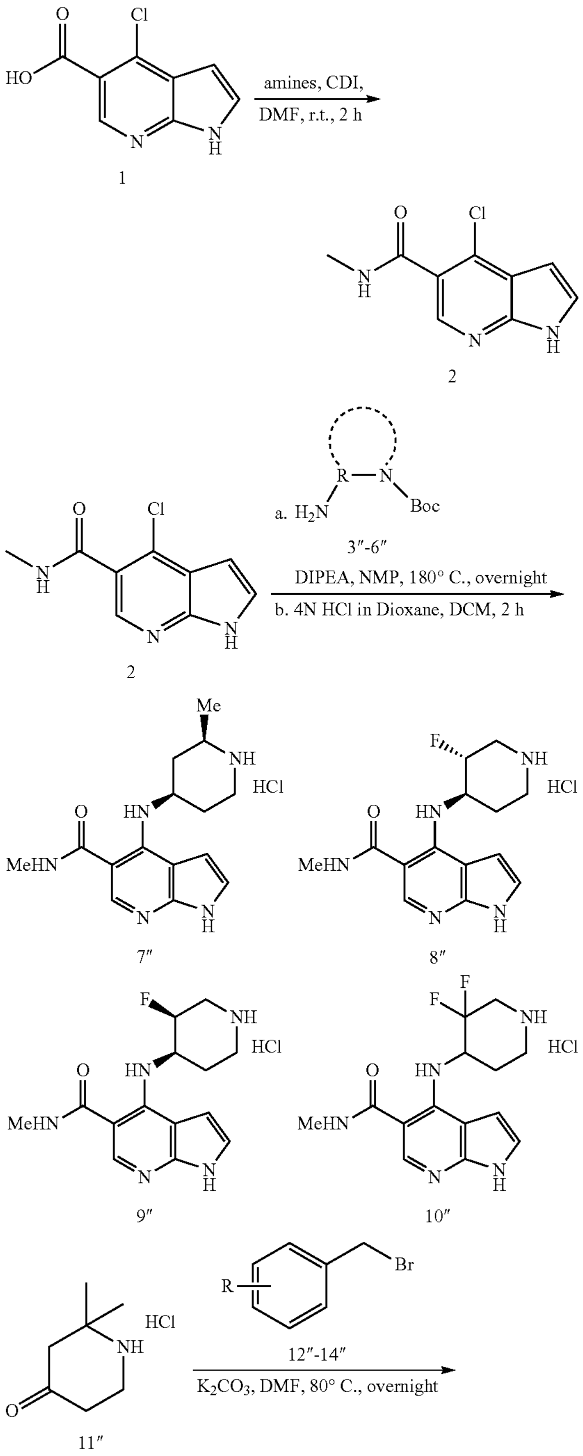

-continued

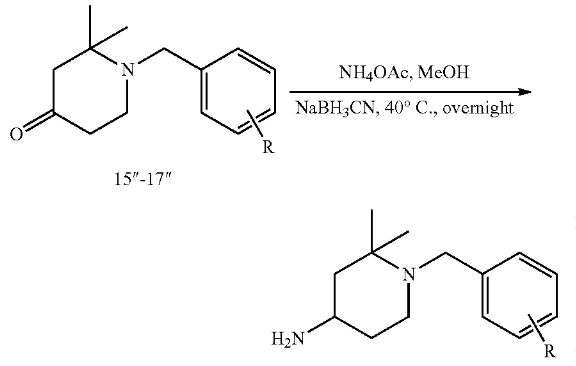

15″-17″

18″-20″

R: H, 3-Cl, 4-Cl, 3-OMe, 4-OMe, 3-CN, 4-CN

As depicted in General Scheme III, an N-alkylated 1-H-pyrrolo[2,3-b]pyridine carboxamides 2 was synthesized by carbonyldiimidazole-mediated amide coupling of 4-chloro-1H-pyrrolo[2,3-b]pyridine-5-carboxylic acid. Compound 2 was reacted with various Boc-protected amines to provide intermediates. In situ deprotection of the Boc protecting groups from the intermediates by treatment with HCl/MeOH and subsequent reductive amination with various benzaldehydes gave final product 21"-24" in high yields. 2-Dimethylpiperidine derivatives were synthesized by carrying out the reactions in the reverse order. Benzyl group-introduced amine intermediates 18"-20" were synthesized by the introduction of a benzyl group into the starting material 11" and subsequent amination of the ketone. Compound 2 was allowed to react with the amines 18"-20" to give desired products 21"-25".

[General Scheme IV]-Experimental procedure for synthesis of final products 21″-25″

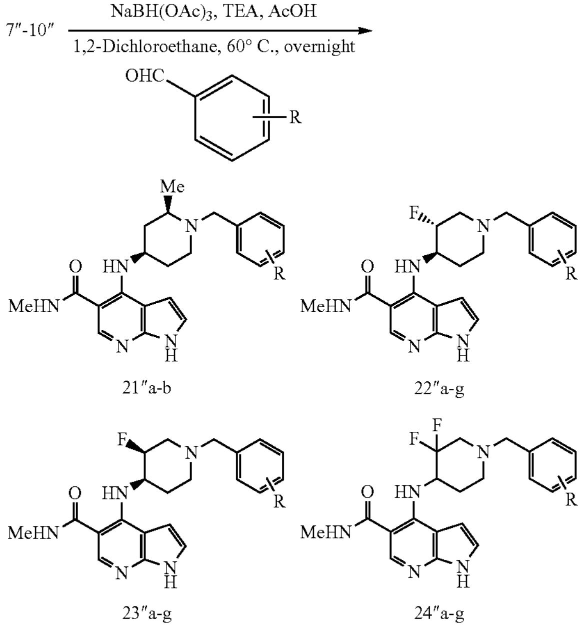

21″a-b

22″a-g

23″a-g

24″a-g

-continued

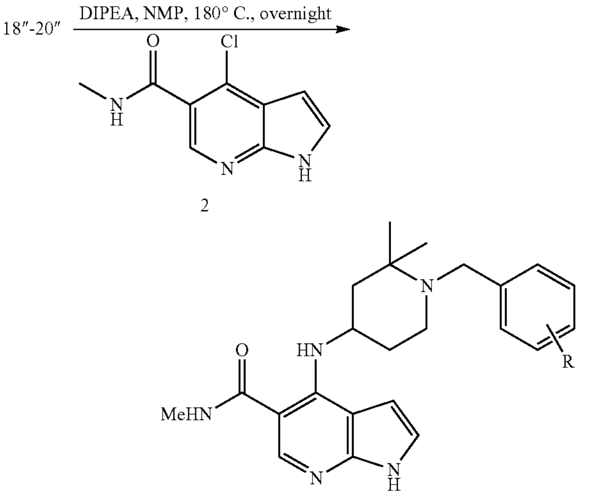

2

25″a-c

General Procedure F

4-Chloro-1H-pyrrolo[2,3-b]pyridine-5-carboxylic acid (1 eq) and CDI (1.05 eq) were added dropwise to a DMF (20 ml) solution at room temperature under a $N_2$ gas atmosphere. The mixture was stirred at the same temperature for 1 h. To the reaction mixture was slowly added dropwise methylamine (5 eq). The resulting mixture was stirred at room temperature for 1 h. The completion of the reaction was confirmed by TLC monitoring and the DMF solvent was removed using a rotary evaporator. Ethyl acetate was poured into the resulting mixture and the precipitate was collected by filtration. Water was poured into the precipitate to remove the imidazole. Filtration afforded a product as a white solid.

4-Chloro-N-methyl-1H-pyrrolo[2,3-b]pyridine-5-carboxamide 2

The title compound was synthesized according to General procedure F. Yield: 86.5%; $^1$H NMR (400 MHz, DMSO-$d_6$) δ 12.15 (s, 1H), 8.37 (q, J=4.7 Hz, 1H), 8.24 (s, 1H), 7.65 (d, J=3.5 Hz, 1H), 6.56 (d, J=3.4 Hz, 1H), 2.80 (d, J=4.6 Hz, 3H); $^{13}$C NMR (101 MHz, Chloroform-d) S 168.85, 149.42, 143.10, 134.32, 128.48, 124.54, 120.69, 100.59, 26.93; MS (ESI, m/z) calculated for $C_9H_8ClN_3O$ $[M+H]^+$ 209.04, found 210.00.

General Procedure G

DIEA (2 eq) and 4-chloro-N-methyl-1H-pyrrolo[2,3-b]pyridine-5-carboxamide (1.0 mmol) were added dropwise to a solution of amine 3"-6" (2 eq) in NMP (2 ml). The mixture was stirred at 180° C. overnight. The resulting mixture was cooled to room temperature, diluted with ethyl acetate, washed with $H_2O$ and brine, and dried over $MgSO_4$. The crude mixture was purified by silica gel flash chromatography (dichloromethane:MeOH=10:1 elution) to obtain a mixture of protected and unprotected products. To the mixture was added dropwise 4 N HCl in dioxane (2 mL). The resulting mixture was stirred at room temperature for 1 h for in situ Boc deprotection. After evaporation and further drying under high vacuum, the resulting product 7"-10" was used in the next step without further purification.

N-Methyl-4-((cis-2-methylpiperidin-4-yl)amino)-1H-pyrrolo[2,3-b]pyridine-5-carboxamide hydrochloride 7"

The title compound was synthesized according to General procedure G. Yield: 37.6%; $^1$H NMR (400 MHz, Deuterium Oxide) δ 8.10 (d, J=0.9 Hz, 1H), 7.19 (dd, J=3.7, 0.8 Hz, 1H), 6.51 (dd, J=3.8, 0.9 Hz, 1H), 4.43-4.37 (m, 1H), 3.51-3.41 (m, 1H), 3.42-3.35 (m, 1H), 3.23-3.11 (m, 1H), 2.90 (d, J=0.8 Hz, 3H), 2.15-2.00 (m, 2H), 1.99-1.88 (m, 1H), 1.48-1.43 (m, 1H), 1.35 (d, J=6.5 Hz, 3H); $^{13}C$ NMR (101 MHz, Deuterium Oxide) S 171.4, 148.6, 148.5, 143.5, 122.4, 104.9, 103.1, 101.7, 47.6, 44.2, 39.0, 34.6, 27.5, 26.7, 26.0; HRMS (ESI, m/z) calculated for $C_{15}H_{21}N_5O$ [M+H]$^+$ 288.1819 found 288.1821.

4-((trans-3-Fluoropiperidin-4-yl)amino)-N-methyl-1H-pyrrolo[2,3-b]pyridine-5-carboxamide hydrochloride 8"

The title compound was synthesized according to General procedure G. Yield: 71%; $^1H$ NMR (400 MHz, Methanol-d$_4$) δ 8.46 (s, 1H), 7.40 (d, J=3.7 Hz, 1H), 7.01 (d, J=3.7 Hz, 1H), 5.17-5.06 (m, 1H), 5.04-4.94 (m, 1H), 3.63-3.57 (m, 2H), 2.93 (s, 3H), 2.61-2.49 (m, 2H), 2.17-2.06 (m, 2H); $^{13}C$ NMR (101 MHz, Methanol-d$_4$) δ 169.32, 154.26, 139.88, 135.89, 125.50, 108.37, 106.48, 105.19, 87.31 (d, $J_{C-F}$=181.0 Hz), 51.81 (d, $J_{C-F}$=23.8 Hz), 44.84 (d, $J_{C-F}$=26.3 Hz), 41.59, 26.80, 26.24; MS (ESI, m/z) calculated for $C_{14}H_{18}FN_5O$ [M+H]$^+$ 292.16 found 292.10.

4-((cis-3-Fluoropiperidin-4-yl)amino)-N-methyl-1H-pyrrolo[2,3-b]pyridine-5-carboxamide hydrochloride 9"

The title compound was synthesized according to General procedure G. Yield: 79%; $^1H$ NMR (400 MHz, DMSO-d$_6$) δ 11.52 (s, 1H), 9.59 (d, J=8.7 Hz, 1H), 8.31 (s, 1H), 8.23 (d, J=4.4 Hz, 1H), 7.16 (d, J=3.5 Hz, 1H), 6.53 (d, J=3.6 Hz, 1H), 4.71 (d, J=50.5 Hz, 1H), 4.34-4.14 (m, 1H), 3.12 (t, J=11.4 Hz, 1H), 2.90 (d, J=14.9 Hz, 1H), 2.84-2.76 (m, 1H), 2.74 (d, J=4.4 Hz, 3H), 2.65 (t, J=12.0 Hz, 1H), 1.86-1.75 (m, 1H), 1.67-1.51 (m, 2H); $^{13}C$ NMR (101 MHz, DMSO-d$_6$) δ 170.02, 150.34, 148.53, 144.51, 122.04, 104.62, 103.13, 101.54, 88.88 (d, $J_{C-F}$=173.6 Hz), 51.71 (d, $J_{C-F}$=18.1 Hz), 48.23 (d, $J_{C-F}$=20.5 Hz), 29.62, 28.05, 26.09; MS (ESI, m/z) calculated for $C_{14}H_{18}FN_5O$ [M+H]$^+$ 292.16 found 292.10.

4-((3,3-Difluoropiperidin-4-yl)amino)-N-methyl-1H-pyrrolo[2,3-b]pyridine-5-carboxamide hydrochloride 10"

The title compound was synthesized according to General procedure G. Yield: 89%; $^1H$ NMR (400 MHz, Chloroform-d) δ 12.09 (s, 1H), 8.93 (s, 1H), 8.54 (d, J=4.7 Hz, 1H), 7.38 (d, J=3.6 Hz, 1H), 6.63 (d, J=3.6 Hz, 1H), 3.92-3.82 (m, 1H), 3.59-3.51 (m, 1H), 3.49 (s, 3H), 3.31 (t, J=11.0 Hz, 1H), 3.27-3.16 (m, 1H), 3.03 (d, J=4.8 Hz, 3H), 2.20-2.10 (m, 1H), 1.78-1.69 (m, 1H), 1.46 (d, J=6.5 Hz, 1H); $^{13}C$ NMR (101 MHz, Chloroform-d) δ 167.37, 151.57, 149.10, 146.45, 125.61, 122.48 (t, $J_{C-F}$=244.4 Hz), 116.47, 114.41, 100.57, 55.10 (dd, $J_{C-F}$=31.5, 26.4 Hz), 52.38 (t, $J_{C-F}$=22.8 Hz), 51.17, 31.20, 26.33; MS (ESI, m/z) calculated for $C_{14}H_{17}F_2N_5O$ [M+H]$^+$ 310.15 found 310.10.

General Procedure H $K_2CO_3$ (5.2 mmol) and benzyl bromide (2.6 mmol) were added dropwise to a solution of 2,2-dimethylpiperidin-4-one (1.3 mmol) in DMF (5 ml). The mixture was stirred at 80° C. overnight. The resulting mixture was poured into DCM (40 ml), washed with $H_2O$ (40 ml) and brine (40 ml), and dried over $MgSO_4$. The crude mixture was purified by silica gel flash chromatography (30% ethyl acetate in n-hexane elution) to obtain a desired product 15"-17". For the conversion of the carbonyl group of the intermediate 15"-17", ammonium acetate (10 eq) and 4 Å molecular sieves were added dropwise to the intermediate 15"-17" (1 eq) in methanol (10 ml). The mixture was stirred for 1 h. To the mixture was added dropwise sodium cyanoborohydride (2 eq). The resulting mixture was stirred at room temperature overnight. The reaction solution was poured into DCM (40 ml), washed with $H_2O$ (40 ml), and dried over $MgSO_4$. The crude mixture was purified by silica gel flash chromatography (dichloromethane:methanol=10:1) to afford an amine compound 18"-20".

1-Benzyl-2,2-dimethylpiperidin-4-one 15"

The title compound was synthesized according to General procedure H. Yield: 41.4%; $^1H$ NMR (400 MHz, Chloroform-d) δ 7.39 (d, J=7.1 Hz, 2H), 7.33 (t, J=7.4 Hz, 2H), 7.25 (t, J=7.2 Hz, 1H), 3.63 (s, 2H), 2.76 (t, J=6.3 Hz, 2H), 2.39 (s, 2H), 2.36-2.28 (m, 2H), 1.19 (s, 6H); $^{13}C$ NMR (101 MHz, Chloroform-d) δ 210.35, 140.46, 128.43, 128.40, 127.01, 57.79, 55.61, 52.92, 46.29, 41.62, 24.07; MS (ESI, m/z) calculated for $C_{14}H_{19}NO$ [M+H]$^+$ 218.15 found 218.10.

1-(3-Chlorobenzyl)-2,2-dimethylpiperidin-4-one 16"

The title compound was synthesized according to General procedure H. Yield: 45.6%; $^1H$ NMR (400 MHz, Chloroform-d) δ 7.43-7.40 (m, 1H), 7.27-7.21 (m, 3H), 3.61 (s, 2H), 2.75 (t, J=6.3 Hz, 2H), 2.39 (s, 2H), 2.34 (dd, J=6.4, 1.4 Hz, 2H), 1.18 (s, 6H); $^{13}C$ NMR (101 MHz, Chloroform-d) δ 210.02, 142.80, 134.45, 129.68, 128.32, 127.23, 126.47, 57.84, 55.55, 52.58, 46.51, 41.59, 24.09; MS (ESI, m/z) calculated for $C_{14}H_{18}ClNO$ [M+H]$^+$ 252.12 found 252.05.

1-(4-Chlorobenzyl)-2,2-dimethylpiperidin-4-one 17"

The title compound was synthesized according to General procedure H. Yield: 54.5%; $^1H$ NMR (400 MHz, Chloroform-d) δ 7.35-7.27 (m, 4H), 3.59 (s, 2H), 2.73 (t, J=6.3 Hz, 2H), 2.38 (s, 2H), 2.36-2.29 (m, 2H), 1.18 (s, 6H); $^{13}C$ NMR (101 MHz, Chloroform-d) δ 210.03, 139.02, 132.63, 129.67, 128.57, 57.81, 55.56, 52.33, 46.34, 41.58, 24.08; MS (ESI, m/z) calculated for $C_{14}H_{18}ClNO$ [M+H]$^+$ 252.12 found 252.05.

1-Benzyl-2,2-dimethylpiperidin-4-amine 18"

The title compound was synthesized according to General procedure H. Yield: 85.8%; $^1H$ NMR (400 MHz, Methanol-d$_4$) δ 7.33-7.22 (m, 4H), 7.19 (t, J=7.1 Hz, 1H), 3.49 (dd, J=435.5, 13.5 Hz, 2H), 2.88-2.77 (m, 1H), 2.61-2.50 (m, 1H), 2.35-2.23 (m, 1H), 1.74-1.59 (m, 2H), 1.33 (t, J=12.2 Hz, 1H), 1.27 (d, J=3.6 Hz, 3H), 1.23-1.11 (m, 1H), 1.06 (s, 3H); $^{13}C$ NMR (101 MHz, Methanol-d$_4$) δ 141.75, 129.97, 129.13, 127.74, 55.37, 54.73, 50.65, 47.02, 46.60, 36.70, 31.21, 16.36; MS (ESI, m/z) calculated for $C_{14}H_{22}N_2$[M+H]$^+$ 219.19 found 219.15.

1-(3-Chlorobenzyl)-2,2-dimethylpiperidin-4-amine 19"

The title compound was synthesized according to General procedure H. Yield: 98.0%; $^1H$ NMR (400 MHz, Methanol-d$_4$) δ 7.37 (s, 1H), 7.28-7.23 (m, 2H), 7.23-7.19 (m, 1H), 3.51 (dd, J=422.1, 14.1 Hz, 2H), 2.90-2.81 (m, 1H), 2.58-

2.49 (m, 1H), 2.40-2.30 (m, 1H), 1.78-1.71 (m, 1H), 1.71-1.65 (m, 1H), 1.35 (t, J=12.2 Hz, 1H), 1.26 (d, J=2.9 Hz, 3H), 1.23-1.16 (m, 1H), 1.07 (s, 3H); $^{13}C$ NMR (101 MHz, Methanol-$d_4$) δ 144.78, 135.13, 130.61, 129.45, 128.00, 127.75, 55.30, 54.17, 50.67, 47.23, 46.61, 36.81, 31.26, 16.44; MS (ESI, m/z) calculated for $C_{14}H_{21}ClN_2$ [M+H]$^+$ 253.15 found 253.10.

1-(4-Chlorobenzyl)-2,2-dimethylpiperidin-4-amine 20"

The title compound was synthesized according to General procedure H. Yield: 93.9%; $^1H$ NMR (400 MHz, Methanol-$d_4$) δ 7.28 (q, J=8.7 Hz, 4H), 3.47 (dd, J=418.1, 13.9 Hz, 2H), 2.89-2.78 (m, 1H), 2.56-2.43 (m, 1H), 2.33-2.24 (m, 1H), 1.76-1.61 (m, 2H), 1.36-1.27 (m, 1H), 1.24 (s, 3H), 1.21-1.10 (m, 1H), 1.05 (s, 3H); $^{13}C$ NMR (101 MHz, Methanol-$d_4$) δ 140.91, 133.26, 131.22, 129.16, 55.29, 53.92, 50.62, 47.08, 46.59, 36.74, 31.25, 16.39; MS (ESI, m/z) calculated for $C_{14}H_{21}ClN_2$ [M+H]$^+$ 253.15 found 253.10.

General Procedure I

Triethylamine (1.1 eq), acetic acid (1.5 eq), and sodium triacetoxyborohydride (2 eq) were added dropwise to an appropriate solution of the deprotected intermediate 7"-10" (0.25 mmol) and benzaldehyde (0.5 mmol) in DCM (5 ml) with stirring at 60° C. for 24 h. The resulting mixture was washed with a saturated aqueous solution of $NaHCO_3$, diluted with ethyl acetate, washed with $H_2O$ and brine, and dried over $MgSO_4$. The crude mixture was purified by silica gel flash chromatography (dichloromethane:MeOH=10:1 elution) to afford a title compound 21"a-b, 22"a-g, 23"a-g, 24"a-g.

4-((cis-1-((5-Chloropyridin-2-yl)methyl)-2-methylpiperidin-4-yl)amino)-N-methyl-1H-pyrrolo[2,3-b]pyridine-5-carboxamide 21"a The title compound was synthesized according to General procedure I. Yield: 40.5%; $^1H$ NMR (400 MHz, Chloroform-d) δ 9.16 (d, J=7.9 Hz, 1H), 8.49 (d, J=2.1 Hz, 1H), 8.23 (s, 1H), 7.65 (dd, J=8.4, 2.5 Hz, 1H), 7.46 (d, J=8.4 Hz, 1H), 7.02 (d, J=3.6 Hz, 1H), 6.51 (s, 1H), 6.49 (d, J=3.7 Hz, 1H), 4.01-3.89 (m, 1H), 3.77 (dd, J=296.5, 14.7 Hz, 2H), 2.96 (d, J=4.7 Hz, 3H), 2.91-2.84 (m, 1H), 2.55-2.43 (m, 1H), 2.32-2.23 (m, 1H), 2.21-2.06 (m, 2H), 1.70-1.44 (m, 2H), 1.19 (d, J=6.1 Hz, 3H); $^{13}C$ NMR (101 MHz, Chloroform-d) δ 170.60, 158.42, 149.99, 149.33, 147.74, 142.87, 136.24, 130.16, 123.77, 121.27, 105.20, 103.59, 102.71, 58.88, 56.20, 52.44, 51.19, 42.31, 33.58, 26.60, 21.19; HRMS (ESI, m/z) calculated for $C_{21}H_{25}ClN_6O$ [M+H]$^+$ 413.1851 found 413.1853.

4-((cis-1-((6-Chloropyridin-3-yl)methyl)-2-methylpiperidin-4-yl)amino)-N-methyl-1H-pyrrolo[2,3-b]pyridine-5-carboxamide 21"b The title compound was synthesized according to General procedure I. Yield: 62.1%; $^1H$ NMR (400 MHz, Chloroform-d) δ 9.16 (d, J=7.7 Hz, 1H), 8.30 (d, J=2.0 Hz, 1H), 8.22 (s, 1H), 7.68 (dd, J=8.2, 2.3 Hz, 1H), 7.30 (d, J=8.2 Hz, 1H), 7.03 (d, J=3.5 Hz, 1H), 6.52 (s, 1H), 6.48 (d, J=3.7 Hz, 1H), 4.01-3.85 (m, 1H), 3.61 (dd, J=365.0, 14.0 Hz, 2H), 2.96 (d, J=4.7 Hz, 3H), 2.81 (dd, J=8.8, 3.2 Hz, 1H), 2.44 (dd, J=8.4, 6.0 Hz, 1H), 2.18-2.05 (m, 3H), 1.62-1.44 (m, 2H), 1.22 (d, J=6.0 Hz, 3H); $^{13}C$ NMR (101 MHz, Chloroform-d) δ 170.59, 150.03, 149.96, 149.76, 149.32, 142.96, 139.39, 133.94, 124.07, 121.28, 105.18, 103.62, 102.68, 56.05, 54.02, 51.59, 51.10, 42.22, 33.37, 26.59, 21.19; HRMS (ESI, m/z) calculated for $C_{21}H_{25}ClN_6O$ [M+H]$^+$ 413.1851 found 413.1853.

4-((trans-1-Benzyl-3-fluoropiperidin-4-yl)amino)-N-methyl-1H-pyrrolo[2,3-b]pyridine-5-carboxamide 22"a The title compound was synthesized according to General procedure I. Yield: 55.8%; $^1H$ NMR (400 MHz, Chloroform-d) δ 11.20 (s, 1H), 9.36 (d, J=8.2 Hz, 1H), 8.25 (d, J=3.8 Hz, 1H), 7.34 (s, 1H), 7.33 (s, 2H), 7.32-7.23 (m, 2H), 7.05 (d, J=3.6 Hz, 1H), 6.59 (d, J=3.5 Hz, 1H), 6.31-6.17 (m, 1H), 4.78-4.54 (m, 1H), 4.32-4.17 (m, 1H), 3.60 (s, 2H), 3.11-3.04 (m, 1H), 2.98 (d, J=4.7 Hz, 3H), 2.80-2.71 (m, 1H), 2.54-2.42 (m, 1H), 2.37 (t, J=9.5 Hz, 1H), 2.31-2.22 (m, 1H), 1.80-1.67 (m, 1H); $^{13}C$ NMR (101 MHz, Chloroform-d) δ 170.82, 150.67, 150.25, 143.38, 137.82, 128.98, 128.36, 127.27, 121.42, 105.41, 103.95, 102.48, 90.63 (d, $J_{C-F}$=180.1 Hz), 62.42, 55.43 (d, $J_{C-F}$=23.6 Hz), 53.96 (d, $J_{C-F}$=23.0 Hz), 50.46, 30.17, 26.66; HRMS (ESI, m/z) calculated $C_{21}H_{24}FN_5O$ [M+H]$^+$ 382.2038 found 382.2041.

4-((trans-1-(3-Chlorobenzyl)-3-fluoropiperidin-4-yl)amino)-N-methyl-1H-pyrrolo[2,3-b]pyridine-5-carboxamide 22"b The title compound was synthesized according to General procedure I. Yield: 24.6%; $^1H$ NMR (400 MHz, Chloroform-d) δ 10.7 (s, 1H), 9.5 (d, J=8.0 Hz, 1H), 8.3 (s, 1H), 7.4 (s, 1H), 7.3-7.2 (m, 3H), 7.0 (d, J=3.5 Hz, 1H), 6.5 (d, J=3.5 Hz, 1H), 6.0 (s, 1H), 4.4-4.3 (m, 1H), 3.7-3.6 (m, 2H), 2.8-2.6 (m, 4H), 2.2-2.1 (m, 2H), 2.04-1.99 (m, 1H), 1.8-1.6 (m, 1H); $^{13}C$ NMR (101 MHz, Chloroform-d) δ 170.83, 150.22, 149.30, 143.33, 139.77, 134.27, 129.65, 128.97, 127.50, 127.11, 121.59, 105.51, 104.02, 102.34, 90.21 (d, $J_{C-F}$=182.0 Hz), 61.76, 55.13 (d, $J_{C-F}$=23.9 Hz), 53.48 (d, $J_{C-F}$=23.7 Hz), 50.22, 29.75, 26.36; HRMS (ESI, m/z) calculated for $C_{21}H_{23}ClFN_5O$ [M+H]$^+$ 416.1648 found 416.1648.

4-((trans-1-(4-Chlorobenzyl)-3-fluoropiperidin-4-yl)amino)-N-methyl-1H-pyrrolo[2,3-b]pyridine-5-carboxamide 22"c The title compound was synthesized according to General procedure I. Yield: 65.6%; $^1H$ NMR (400 MHz, Chloroform-d) δ 11.37 (s, 1H), 9.38 (d, J=8.2 Hz, 1H), 8.25 (d, J=4.1 Hz, 1H), 7.34-7.21 (m, 4H), 7.04 (d, J=3.1 Hz, 1H), 6.57 (d, J=3.4 Hz, 1H), 6.30 (s, 1H), 4.74-4.55 (m, 1H), 4.32-4.19 (m, 1H), 3.55 (s, 2H), 3.02 (d, J=14.5 Hz, 1H), 2.98 (d, J=4.7 Hz, 3H), 2.75-2.67 (m, 1H), 2.56-2.43 (m, 1H), 2.37 (t, J=9.0 Hz, 1H), 2.33-2.21 (m, 1H), 1.81-1.67 (m, 1H); $^{13}C$ NMR (101 MHz, Chloroform-d) δ 170.78, 150.23, 143.23, 143.16, 136.40, 132.97, 130.19, 128.52, 121.54, 105.43, 103.91, 102.37, 90.37 (d, $J_{C-F}$=179.6 Hz), 61.59, 55.22 (d, $J_{C-F}$=23.8 Hz), 53.61 (d, $J_{C-F}$=24.1 Hz), 50.23, 29.95, 26.66; HRMS (ESI, m/z) calculated for $C_{21}H_{23}ClFN_5O_2$ [M+H]$^+$ 416.1648 found 416.1651.

4-((trans-1-(3-Methoxybenzyl)-3-fluoropiperidin-4-yl)amino)-N-methyl-1H-pyrrolo[2,3-b]pyridine-5-carboxamide 22"d The title compound was synthesized according to General procedure I. Yield: 61.3%; $^1H$ NMR (400 MHz, Chloroform-d) δ 11.40 (s, 1H), 9.36 (d, J=8.2 Hz, 1H), 8.24 (d, J=5.6 Hz, 1H), 7.28-7.17 (m, 1H), 7.08-6.96 (m, 1H), 6.94-6.87 (m, 2H), 6.81 (dd, J=8.9, 1.8 Hz, 1H), 6.56 (d, J=3.0 Hz, 1H), 6.30 (s, 1H), 4.77-4.55 (m, 1H), 4.34-4.15 (m, 1H), 3.81 (s, 3H), 3.57 (s, 2H), 3.10 (td, J=15.5, 13.4, 6.8 Hz, 1H), 2.97 (d, J=4.7 Hz, 3H), 2.82-2.75 (m, 1H), 2.47 (q, J=7.1 Hz, 1H), 2.35 (t, J=9.5 Hz, 1H), 2.26 (d, J=5.3 Hz, 1H), 1.85-1.68 (m, 1H); $^{13}$C NMR (101 MHz, Chloroform-d) δ 170.79, 159.75, 150.30, 143.17, 143.02, 139.55, 129.31, 121.50, 121.23, 114.21, 112.85, 105.42, 103.94, 102.41, 90.68 (d, $J_{C-F}$=180.1 Hz), 62.31, 55.50 (d, $J_{C-F}$=24.1 Hz), 55.23, 54.16 (d, $J_{C-F}$=22.8 Hz), 50.53, 30.27, 26.65; HRMS (ESI, m/z) calculated for $C_{22}H_{26}FN_5O_2$ [M+H]$^+$ 412.2143 found 412.2139.

4-((trans-1-(4-Methoxybenzyl)-3-fluoropiperidin-4-yl)amino)-N-methyl-1H-pyrrolo[2,3-b]pyridine-5-carboxamide 22"e The title compound was synthesized according to General procedure I. Yield: 69.2%; $^1$H NMR (400 MHz, Chloroform-d) δ 11.23 (s, 1H), 9.35 (d, J=8.2 Hz, 1H), 8.24 (d, J=4.1 Hz, 1H), 7.23 (d, J=8.5 Hz), 2H), 7.06-6.97 (m, 1H), 6.87 (d, J=8.6 Hz, 2H), 6.56 (d, J=3.2 Hz, 1H), 6.34 (s, 1H), 4.74-4.54 (m, 1H), 4.26-4.08 (m, 1H), 3.80 (s, 3H), 3.53 (s, 2H), 3.07 (d, J=5.1 Hz, 1H), 2.97 (d, J=4.7 Hz, 3H), 2.79-2.69 (m, 1H), 2.44 (d, J=10.5 Hz, 1H), 2.33 (t, J=9.4 Hz, 1H), 2.29-2.19 (m, 1H), 1.79-1.66 (m, 1H); $^{13}$C NMR (101 MHz, Chloroform-d) δ 170.78, 150.23, 143.23, 143.16, 136.40, 132.97, 130.19, 128.52, 121.54, 105.43, 103.91, 102.37, 90.37 (d, $J_{C-F}$=178.4 Hz), 61.59, 60.43, 55.22 (d, $J_{C-F}$=23.1 Hz), 53.61 (d, $J_{C-F}$=17.6 Hz), 50.23, 29.95, 26.66; HRMS (ESI, m/z) calculated for $C_{22}H_{26}FN_5O$ [M+H]$^+$ 412.2143 found 412.2146.

4-((trans-1-(3-Cyanobenzyl)-3-fluoropiperidin-4-yl)amino)-N-methyl-1H-pyrrolo[2,3-b]pyridine-5-carboxamide 22"f The title compound was synthesized according to General procedure I. Yield: 59.1%; $^1$H NMR (400 MHz, Chloroform-d) δ 11.19 (s, 1H), 9.42 (d, J=8.2 Hz, 1H), 8.27 (s, 1H), 7.64 (s, 1H), 7.62-7.52 (m, 2H), 7.44 (t, J=7.7 Hz, 1H), 7.09 (d, J=3.6 Hz, 1H), 6.60 (d, J=3.7 Hz, 1H), 6.28 (d, J=4.7 Hz, 1H), 4.78-4.55 (m, 1H), 4.34-4.25 (m, 1H), 3.61 (s, 2H), 2.99 (d, J=4.7 Hz, 3H), 3.03-2.90 (m, 1H), 2.71 (s, 1H), 2.61-2.50 (m, 1H), 2.43 (t, J=8.7 Hz, 1H), 2.36-2.25 (m, 1H), 1.84-1.73 (m, 1H); $^{13}$C NMR (101 MHz, Chloroform-d) δ 170.91, 150.79, 150.25, 143.52, 139.82, 133.28, 132.32, 131.17, 129.34, 121.68, 119.00, 112.60, 105.55, 104.04, 102.48, 90.09 (d, $J_{C-F}$=180.0 Hz), 60.53, 55.14 (d, $J_{C-F}$=22.5 Hz), 53.19 (d, $J_{C-F}$=18.6 Hz), 50.16, 29.81, 26.78; HRMS (ESI, m/z) calculated for $C_{22}H_{23}FN_6O$ [M+H]$^+$ 407.1990 found 407.1995.

4-((trans-1-(4-Cyanobenzyl)-3-fluoropiperidin-4-yl)amino)-N-methyl-1H-pyrrolo[2,3-b]pyridine-5-carboxamide 22"g The title compound was synthesized according to General procedure I. Yield: 55.8%; $^1$H NMR (400 MHz, Chloroform-d) δ 11.40 (s, 1H), 9.43 (d, J=8.2 Hz, 1H), 8.27 (s, 1H), 7.62 (d, J=8.2 Hz, 2H), 7.45 (d, J=8.1 Hz, 2H), 7.07 (d, J=3.5 Hz, 1H), 6.58 (d, J=3.4 Hz, 1H), 6.32 (s, 1H), 4.79-4.54 (m, 1H), 4.28 (d, J=4.8 Hz, 1H), 3.63 (s, 2H), 3.10-2.91 (m, 1H), 2.99 (d, J=4.7 Hz, 3H), 2.70 (s, 1H), 2.61-2.49 (m, 1H), 2.42 (t, J=8.7 Hz, 1H), 2.37-2.23 (m, 1H), 1.84-1.70 (m, 1H); $^{13}$C NMR (101 MHz, Chloroform-d) δ 170.88, 150.61, 150.28, 143.88, 143.33, 132.35, 129.37, 121.75, 119.02, 111.19, 105.56, 103.99, 102.40, 90.12 (d, $J_{C-F}$=179.6 Hz), 61.86 Hz, 55.19 (d, $J_{C-F}$=23.6 Hz), 53.17 (d, $J_{C-F}$=25.0 Hz), 50.24, 29.80, 26.77; HRMS (ESI, m/z) calculated for $C_{22}H_{23}FN_6O$ [M+H]$^+$ 407.1990 found 407.1996.

4-((cis-1-Benzyl-3-fluoropiperidin-4-yl)amino)-N-methyl-1H-pyrrolo[2,3-b]pyridine-5-carboxamide 23"a The title compound was synthesized according to General procedure I. Yield: 26.0%; $^1$H NMR (400 MHz, Chloroform-d) 10.99 (s, 1H), 9.45 (d, J=8.4 Hz, 1H), 8.25 (s, 1H), 7.37-7.31 (m, 4H), 7.29-7.26 (m, 1H), 7.07 (d, J=3.6 Hz, 1H), 6.44 (d, J=3.7 Hz, 1H), 6.15 (d, J=4.6 Hz, 1H), 4.87 (d, J=48.3 Hz, 1H), 4.33-4.05 (m, 1H), 3.63 (s, 2H), 3.20 (s, 1H), 2.99 (d, J=4.8 Hz, 3H), 2.91 (d, J=10.0 Hz, 1H), 2.54-2.37 (m, 1H), 2.32 (t, J=10.6 Hz, 1H), 2.16-2.05 (m, 1H), 2.05-1.98 (m, 1H); $^{13}$C NMR (101 MHz, Chloroform-d) δ 170.82, 150.67, 150.25, 143.38, 137.82, 128.98, 128.36, 127.27, 121.42, 105.41, 103.95, 102.48, 88.25 (d, $J_{C-F}$=180.1 Hz), 62.42, 55.13 (d, $J_{C-F}$=22.2 Hz), 52.53 (d, $J_{C-F}$=19.8 Hz), 50.46, 30.17, 26.66; HRMS (ESI, m/z) calculated $C_{21}H_{24}FN_5O$ [M+H]$^+$ 382.2038 found 382.2040.

4-((cis-1-(3-Chlorobenzyl)-3-fluoropiperidin-4-yl)amino)-N-methyl-1H-pyrrolo[2,3-b]pyridine-5-carboxamide 23"b The title compound was synthesized according to General procedure I. Yield: 35.1%; $^1$H NMR (400 MHz, DMSO-$d_6$) δ 12.32 (s, 1H), 10.42 (d, J=8.6 Hz, 1H), 9.11 (s, 1H), 9.04 (d, J=4.5 Hz, 1H), 8.22-8.14 (m, 2H), 8.14-8.04 (m, 2H), 7.96 (d, J=2.1 Hz, 1H), 7.30 (d, J=3.0 Hz, 1H), 5.64 (d, J=49.5 Hz), 1H), 5.10-4.88 (m, 1H), 4.37 (s, 2H), 3.86 (s, 1H), 3.58 (s, 1H), 3.54 (d, J=4.3 Hz, 3H), 3.23 (d, J=12.6 Hz, 1H), 3.12 (t, J=10.7 Hz, 1H), 2.60 (t, J=10.7 Hz, 2H); $^{13}$C NMR (101 MHz, DMSO-$d_6$) δ 169.97, 150.33, 148.69, 144.47, 140.85, 133.00, 130.12, 128.36, 127.36, 126.98, 122.14, 104.65, 103.23, 101.42, 88.59 (d, $J_{C-F}$=177.1 Hz), 60.36, 54.58 (d, $J_{C-F}$=17.6 Hz), 51.33 (d, $J_{C-F}$=17.9 Hz), 50.14, 27.95, 26.09; HRMS (ESI, m/z) calculated for $C_{21}H_{23}ClFN_5O$ [M+H]$^+$ 416.1648 found 416.1648.

4-((cis-1-(4-Chlorobenzyl)-3-fluoropiperidin-4-yl)amino)-N-methyl-1H-pyrrolo[2,3-b]pyridine-5-carboxamide 23"c The title compound was synthesized according to General procedure I. Yield: 35.1%; $^1$H NMR (400 MHz, DMSO-$d_6$) δ 11.52 (s, 1H), 9.63 (d, J=8.7 Hz, 1H), 8.32 (s, 1H), 8.27-8.17 (m, 1H), 7.44-7.30 (m, 4H), 7.17 (dd, J=3.4, 2.4 Hz, 1H), 6.51 (d, J=2.1 Hz, 1H), 4.85 (d, J=49.4 Hz, 1H), 4.29-4.14 (m, 1H), 3.55 (s, 2H), 3.05 (d, J=9.3 Hz, 1H), 2.81-2.77 (m, 1H), 2.75 (d, J=4.4 Hz, 3H), 2.43 (d, J=12.7 Hz, 1H), 2.31 (t, J=11.1 Hz, 1H), 1.90 (d, J=9.1 Hz, 1H), 1.79 (q, J=10.7 Hz, 1H); $^{13}$C NMR (101 MHz, DMSO-$d_6$) δ 170.42, 150.78, 149.15, 144.92, 137.59, 131.97, 131.00, 128.64, 122.56, 105.08, 103.66, 101.86, 89.03 (d, $J_{C-F}$=177.2 Hz), 60.77, 55.03 (d, $J_{C-F}$=20.5 Hz), 51.82 (d, $J_{C-F}$=17.6 Hz), 33.91, 28.37, 26.5; HRMS (ESI, m/z) calculated for $C_{21}H_{23}ClFN_5O$ [M+H]$^+$ 416.1648 found 416.1648.

4-((cis-1-(3-Methoxybenzyl)-3-fluoropiperidin-4-yl)amino)-N-methyl-1H-pyrrolo[2,3-b]pyridine-5-carboxamide 23"d The title compound was synthesized according to General procedure I. Yield: 39.6%; $^1$H NMR (400 MHz, Chloroform-d) δ 9.90 (s, 1H), 9.51 (d, J=8.5 Hz, 1H), 8.21 (s, 1H), 7.23 (d, J=7.8 Hz, 1H), 7.06 (d, J=3.7 Hz, 1H), 6.96-6.90 (m, 2H), 6.84-6.79 (m, 1H), 6.46 (d, J=3.7 Hz, 1H), 6.10 (s, 1H), 4.87 (d, J=48.7 Hz, 1H), 4.18 (d, J=24.4 Hz, 1H), 3.82 (s, 3H), 3.62-3.60 (m, 2H), 3.21 (s, 1H), 3.00 (d, J=4.7 Hz, 3H), 2.96-2.87 (m, 1H), 2.52-2.28 (m, 2H), 2.18-2.06 (m, 2H); $^{13}$C NMR (101 MHz, Methanol-$d_4$) δ 171.69, 160.36, 150.11, 149.89, 144.22, 138.98, 129.85, 122.61, 122.29, 115.30, 113.55, 106.10, 104.87, 102.29, 88.89 (d, $J_{C-F}$=179.0 Hz), 62.71, 55.54 (d, $J_{C-F}$=18.4 Hz), 52.95 (d, $J_{C-F}$=19.3 Hz), 51.56, 30.15, 28.33, 26.62; HRMS (ESI, m/z) calculated for $C_{22}H_{26}FN_5O_2$[M+H]$^+$ 412.2143 found 412.2148.

4-((dis-1-(4-Methoxybenzyl)-3-fluoropiperidin-4-yl)amino)-N-methyl-1H-pyrrolo[2,3-b]pyridine-5-carboxamide 23"e The title compound was synthesized according to General procedure I. Yield: 50.3%; $^1$H NMR (400 MHz, DMSO-$d_6$) δ 11.52 (s, 1H), 9.62 (d, J=8.7 Hz, 1H), 8.31 (s, 1H), 8.27-8.19 (m, 1H), 7.23 (d, J=8.7 Hz, 2H), 7.16 (dd, J=3.3, 2.2 Hz, 1H), 6.95-6.83 (m, 2H), 6.49 (d, J=2.5 Hz, 1H), 4.83 (d, J=49.6 Hz, 1H), 4.26-4.09 (m, 1H), 3.74 (s, 3H), 3.48 (s, 2H), 3.04 (s, 1H), 2.82-2.77 (m, 1H), 2.74 (d, J=4.4 Hz, 3H), 2.48-2.31 (m, 1H), 2.26 (t, J=10.8 Hz, 1H), 1.89 (d, J=9.9 Hz, 1H), 1.76 (q, J=10.9 Hz, 1H); $^{13}$C NMR (101 MHz, DMF-$d_7$) S 169.97, 158.33, 150.32, 148.71, 144.47, 130.06, 129.74, 122.11, 113.59, 104.62, 103.19, 101.41, 88.62 (d, $J_{C-F}$=177.0 Hz), 60.73, 54.99, 54.53 (d, $J_{C-F}$=14.5 Hz), 51.48 (d, $J_{C-F}$=17.5 Hz), 50.05, 27.95, 26.0; HRMS (ESI, m/z) calculated for $C_{22}H_{26}FN_5O_2$[M+H]$^+$ 412.2143 found 412.2148.

4-((cis-1-(3-Cyanobenzyl)-3-fluoropiperidin-4-yl)amino)-N-methyl-1H-pyrrolo[2,3-b]pyridine-5-carboxamide 23"f The title compound was synthesized according to General procedure I. Yield: 49.1%; $^1$H NMR (400 MHz, DMSO-$d_6$) δ 11.52 (s, 1H), 9.63 (d, J=8.7 Hz, 1H), 8.32 (s, 1H), 8.24 (d, J=4.5 Hz, 1H), 7.78-7.72 (m, 2H), 7.69 (d, J=7.9 Hz, 1H), 7.57 (t, J=7.7 Hz, 1H), 7.17 (dd, J=3.2, 2.2 Hz, 1H), 6.51 (d, J=2.4 Hz, 1H), 4.86 (d, J=49.4 Hz, 1H), 4.30-4.14 (m, 1H), 3.63 (s, 2H), 3.06 (t, J=9.3 Hz, 1H), 2.81-2.77 (m, 1H), 2.75 (d, J=4.4 Hz, 3H), 2.51 (dd, J=35.7, 12.9 Hz, 1H), 2.34 (t, J=10.6 Hz, 1H), 1.90 (d, J=9.7 Hz, 1H), 1.80 (q, J=10.7 Hz, 1H); $^{13}$C NMR (101 MHz, DMSO-$d_6$) δ 169.96, 150.32, 148.69, 144.46, 139.93, 133.64, 132.09, 130.90, 129.53, 122.13, 118.93, 111.24, 104.65, 103.24, 101.43, 88.58 (d, $J_{C-F}$=176.9 Hz), 60.02, 54.50 (d, $J_{C-F}$=18.4 Hz), 51.28 (d, $J_{C-F}$=17.9 Hz), 50.04, 27.91, 26.08; HRMS (ESI, m/z) calculated for $C_{22}H_{23}FN_6O$ [M+H]$^+$ 407.1990 found 407.1991.

4-((cis-1-(4-Cyanobenzyl)-3-fluoropiperidin-4-yl)amino)-N-methyl-1H-pyrrolo[2,3-b]pyridine-5-carboxamide 23"g The title compound was synthesized according to General procedure I. Yield: 31.9%; $^1$H NMR (400 MHz, DMSO-$d_6$) δ 11.52 (s, 1H), 9.62 (d, J=8.7 Hz, 1H), 8.31 (s, 1H), 8.24 (d, J=4.6 Hz, 1H), 7.82 (d, J=8.3 Hz, 2H), 7.54 (d, J=8.3 Hz, 2H), 7.17 (dd, J=3.3, 2.4 Hz, 1H), 6.52-6.49 (m, 1H), 4.85 (d, J=49.5 Hz, 1H), 4.29-4.14 (m, 1H), 3.66 (s, 2H), 3.06 (t, J=9.3 Hz, 1H), 2.82-2.76 (m, 1H), 2.74 (d, J=4.4 Hz, 3H), 2.60-2.42 (m, 1H), 2.35 (t, J=10.4 Hz, 1H), 1.90 (d, J=9.8 Hz, 1H), 1.85-1.71 (m, 1H); $^{13}$C NMR (101 MHz, DMSO-$d_6$) δ 169.96, 150.32, 148.68, 144.46, 144.34, 132.23, 129.48, 122.15, 118.95, 109.77, 104.64, 103.23, 101.41, 88.57 (d, $J_{C-F}$=177.1 Hz) 60.50, 54.65 (d, $J_{C-F}$=19.7 Hz), 51.27 (d, $J_{C-F}$=18.0 Hz), 50.17, 27.92, 26.08; HRMS (ESI, m/z) calculated for $C_{22}H_{23}FN_6O$ [M+H]$^+$ 407.1990 found 407.1991.

4-((1-Benzyl-3,3-difluoropiperidin-4-yl)amino)-N-methyl-1H-pyrrolo[2,3-b]pyridine-5-carboxamide 24"a The title compound was synthesized according to General procedure I. Yield: 36.5%; $^1$H NMR (400 MHz, Chloroform-d) δ 12.07 (s, 1H), 8.98 (s, 1H), 8.63 (d, J=4.5 Hz, 1H), 7.41-7.33 (m, 5H), 7.33-7.28 (m, 1H), 6.64 (d, J=3.4 Hz, 1H), 4.01 (s, 2H), 3.94-3.84 (m, 1H), 3.58-3.45 (m, 2H), 3.24-3.08 (m, 2H), 3.02 (d, J=4.8 Hz, 3H), 2.13 (dd, J=8.5, 3.9 Hz, 1H), 1.88-1.76 (m, 1H); $^{13}$C NMR (101 MHz, Chloroform-d) δ 167.24, 151.70, 149.17, 146.66, 139.73, 128.60, 128.08, 127.32, 125.47, 120.7 (t, $J_{C-F}$=247.02 Hz), 116.52, 114.42, 100.67, 56.42 (t, $J_{C-F}$=21.4 Hz), 55.01 (t, $J_{C-F}$=29.4 Hz), 51.59, 30.95, 29.41, 26.29; HRMS (ESI, m/z) calculated for $C_{21}H_{23}F_2N_5O$ [M+H]$^+$ 400.1943 found 400.1946.

4-((1-(3-Chlorobenzyl)-3,3-difluoropiperidin-4-yl)amino)-N-methyl-1H-pyrrolo[2,3-b]pyridine-5-carboxamide 24"b The title compound was synthesized according to General procedure I.—Yield: 60.6%; $^1$H NMR (400 MHz, Chloroform-d) δ 12.30 (s, 1H), 8.96 (s, 1H), 8.66-8.51 (m, 1H), 7.41 (s, 1H), 7.38 (d, J=3.0 Hz, 1H), 7.30-7.24 (m, 4H), 6.63 (d, J=3.3 Hz, 1H), 4.00 (d, J=7.1 Hz, 2H), 3.93-3.82 (m, 1H), 3.59-3.44 (m, 2H), 3.22 (t, J=10.0 Hz, 1H), 3.17-3.06 (m, 1H), 3.03 (d, J=4.8 Hz, 3H), 2.13 (dd, J=9.0, 4.5 Hz, 1H), 1.88-1.77 (m, 1H); $^{13}$C NMR (101 MHz, Chloroform-d) 167.38, 151.80, 149.20, 146.61, 142.09, 134.54, 129.94, 128.24, 127.56, 126.25, 125.70, 120.74 (t, $J_{C-F}$=246.2 Hz), 116.56; 114.54, 100.69, 56.73 (t, $J_{C-F}$=21.5 Hz), 55.25 (t, $J_{C-F}$=29.0 Hz), 51.21, 31.07, 29.80, 26.42; HRMS (ESI, m/z) calculated for $C_{21}H_{22}ClF_2N_5O$ [M+H]$^+$ 434.1554 found 434.1559.

4-((1-(4-Chlorobenzyl)-3,3-difluoropiperidin-4-yl)amino)-N-methyl-1H-pyrrolo[2,3-b]pyridine-5-carboxamide 24"c The title compound was synthesized according to General procedure I. Yield: 60.6%; $^1$H NMR (400 MHz, Methanol-$d_4$) δ 9.84 (s, 1H), 8.91 (dd, J=23.9, 8.5 Hz, 4H), 8.86 (s, 1H), 8.23 (d, J=3.7 Hz, 1H), 5.50 (s, 2H), 5.46-5.35 (m, 2H), 5.25-5.15 (m, 1H), 5.11-4.98 (m, 1H), 4.69-4.57 (m, 1H), 4.50 (s, 3H), 3.72-3.63 (m, 1H), 3.47-3.34 (m, 1H); $^{13}$C NMR (101 MHz, Methanol-$d_4$) δ 171.48, 151.58, 150.61, 145.66, 140.08, 133.83, 130.96, 129.50, 125.90, 121.8 (t, $J_{C-F}$=247.3 Hz), 117.01, 114.62, 101.72, 58.0 (t, $J_{C-F}$=20.8 Hz), 56.2 (t, $J_{C-F}$=29.7 Hz), 51.58, 50.14, 30.46, 26.85; HRMS (ESI, m/z) calculated for $C_{21}H_{22}ClF_2N_5O$ [M+H]$^+$ 434.1554 found 434.11557.

4-((1-(3-Methoxybenzyl)-3,3-difluoropiperidin-4-yl)amino)-N-methyl-1H-pyrrolo[2,3-b]pyridine-5-carboxamide 24"d The title compound was synthesized according to General procedure I. Yield: 60.6%; $^1$H NMR (400 MHz, Chloroform-d) δ 11.72 (s, 1H), 8.98 (s, 1H), 8.60 (s, 1H), 7.38 (s, 1H), 7.28 (d, J=10.4 Hz, 1H), 6.97 (d, J=6.7 Hz, 2H), 6.84 (d, J=8.4 Hz, 1H), 6.65 (s, 1H), 3.99 (s, 2H), 3.95-3.87 (m, 1H), 3.84 (s, 3H), 3.51 (t, J=14.6 Hz, 2H), 3.21 (t, J=10.7 Hz, 1H), 3.14 (d, J=5.7 Hz, 1H), 3.03 (d, J=4.3 Hz, 3H), 2.12 (s, 1H), 1.95-1.79 (m, 1H); $^{13}C$ NMR (101 MHz, Chloroform-d) δ 167.20, 159.85, 151.63, 149.15, 146.77, 141.38, 129.61, 125.35, 120.63 (t, $J_{C-F}$=246.2 Hz), 120.31, 116.58, 114.36, 113.67, 100.75, 56.32 (t, $J_{C-F}$=21.5 Hz), 55.24, 55.03 (t, $J_{C-F}$=29.0 Hz), 50.39, 29.41, 26.29; HRMS (ESI, m/z) calculated for $C_{22}H_{25}F_2N_5O$ $[M+H]^+$ 430.2049 found 430.2057.

4-((1-(4-Methoxybenzyl)-3,3-difluoropiperidin-4-yl)amino)-N-methyl-1H-pyrrolo[2,3-b]pyridine-5-carboxamide 24"e The title compound was synthesized according to General procedure I. Yield: 62.3%; $^1H$ NMR (400 MHz, Chloroform-d) δ 11.83 (s, 1H), 8.98 (s, 1H), 8.61 (d, J=4.7 Hz, 1H), 7.38 (d, J=2.5 Hz, 1H), 7.30 (d, J=8.6 Hz, 2H), 6.95-6.87 (m, 2H), 6.64 (d, J=3.4 Hz, 1H), 3.94 (s, 2H), 3.91-3.84 (m, 1H), 3.82 (s, 3H), 3.55-3.49 (m, 2H), 3.20 (t, J=10.0 Hz, 1H), 3.16-3.06 (m, 1H), 3.02 (d, J=4.8 Hz, 3H), 2.11 (dd, J=8.2, 4.2 Hz, 1H), 1.88-1.78 (m, 1H); $^{13}C$ NMR (101 MHz, Chloroform-d) δ 167.24, 158.90, 151.73, 149.19, 146.80, 131.81, 129.31, 125.38, 120.68 (t, $J_{C-F}$ 247.0 Hz), 116.63, 114.41, 113.99, 100.75, 56.30 (t, $J_{C-F}$=21.5 Hz), 55.32, 55.04 (t, $J_{C-F}$=28.9 Hz), 51.02, 50.35, 29.46, 26.28; HRMS (ESI, m/z) calculated for $C_{22}H_{25}F_2N_5O$ $[M+H]^+$ 430.2049 found 430.2052.

4-((1-(3-Cyanobenzyl)-3,3-difluoropiperidin-4-yl)amino)-N-methyl-1H-pyrrolo[2,3-b]pyridine-5-carboxamide 24"f The title compound was synthesized according to General procedure I. Yield: 30.3%; $^1H$ NMR (400 MHz, Chloroform-d) δ 9.33 (s, 1H), 8.96 (s, 1H), 8.45 (s, 1H), 8.17 (t, J=1.4 Hz, 1H), 8.08-8.00 (m, 1H), 7.82-7.75 (m, 1H), 7.60 (d, J=7.9 Hz, 1H), 7.36 (dd, J=3.6, 2.5 Hz, 1H), 6.75 (dd, J=3.7, 2.0 Hz, 1H), 4.07 (d, J=11.2 Hz, 1H), 3.88 (d, J=10.1 Hz, 2H), 3.69-3.59 (m, 1H), 3.55-3.47 (m, 1H), 3.35-3.27 (m, 1H), 3.07 (d, J=4.0 Hz, 3H), 2.03 (d, J=11.0 Hz, 1H), 1.36-1.26 (m, 4H); HRMS (ESI, m/z) calculated for $C_{22}H_{22}F_2N_6O$ $[M+H]^+$ 425.1896 found 425.1898.

4-((1-(4-Cyanobenzyl)-3,3-difluoropiperidin-4-yl)amino)-N-methyl-1H-pyrrolo[2,3-b]pyridine-5-carboxamide 24"g The title compound was synthesized according to General procedure I. Yield: 58.6%; $^1H$ NMR (400 MHz, Chloroform-d) δ 11.64 (s, 1H), 8.94 (s, 1H), 8.43 (d, J=4.5 Hz, 1H), 7.68-7.65 (m, 2H), 7.53 (d, J=8.4 Hz, 2H), 7.38 (d, J=3.2 Hz, 1H), 6.63 (d, J=3.4 Hz, 1H), 4.18-4.05 (m, 2H), 3.94-3.84 (m, 1H), 3.55-3.47 (m, 2H), 3.25 (t, J=10.4 Hz, 1H), 3.11-3.05 (m, 1H), 3.03 (d, J=4.8 Hz, 3H), 2.17-2.12 (m, 1H), 1.88-1.78 (m, 1H); HRMS (ESI, m/z) calculated for $C_{22}H_{22}F_2N_6O$ $[M+H]^+$ 425.1896 found 425.1897.

General Procedure J

DIEA (10 eq) and 4-chloro-N-methyl-1H-pyrrolo[2,3-b]pyridine-5-carboxamide (0.5 mmol) were added dropwise to a solution of the amine 18"-20" (4 eq) in NNP (2 ml). The mixture was stirred at 180° C. overnight. The resulting mixture was cooled to room temperature, diluted with ethyl acetate, washed with $H_2O$ and brine, and dried over $MgSO_4$. The crude mixture was purified by silica gel flash chromatography (dichloromethane:MeOH=10:1 elution) to afford a title product 25"a-c.

4-((1-Benzyl-2,2-dimethylpiperidin-4-yl)amino)-N-methyl-1H-pyrrolo[2,3-b]pyridine-5-carboxamide 25"a The title compound was synthesized according to General procedure J. Yield: 62.3%; $^1H$ NMR (400 MHz, Chloroform-cd) δ 9.14 (d, J=7.8 Hz, 1H), 8.25 (s, 1H), 7.37 (d, J=7.1 Hz, 2H), 7.31 (t, J=7.4 Hz), 2H), 7.23 (t, J=7.2 Hz, 11H), 6.99 (d, J=3.1 Hz, 1H), 6.56 (s, 11H), 6.53 (d, J=3.3 Hz, 1H), 4.19-4.09 (m, 1H), 3.56 (dd, J=397.7, 14.1 Hz, 2H), 2.98 (d, J=4.7 Hz, 3H), 2.72-2.61 (m, 1H), 2.47-2.34 (m, 1H), 2.11-1.97 (m, 2H), 1.67 (t, J=12.1 Hz, 1H), 1:61-1.49 (m, 1H), 1.27 (s, 3H), 1.18 (s, 3H); $^{13}C$ NMR (101 MHz, Chloroform-d) δ 170.5, 150.1, 142.8, 142.7, 141.1, 128.2, 128.2, 126.6, 121.0, 105.2, 103.7, 102.8, 54.2, 53.3, 48.4, 47.4, 45.5, 34.3, 30.4, 26.6, 16.5; HRMS (ESI, m/z) calculated for $C_{23}H_{29}N_5O$ $[M+H]^+$ 392.2445 found 392.2447.

4-((1-(3-Chlorobenzyl)-2,2-dimethylpiperidin-4-yl)amino)-N-methyl-1H-pyrrolo[2,3-b]pyridine-5-carboxamide 25"b The title compound was synthesized according to General procedure T. Yield: 11.0%; $^1H$ NMR (400 MHz, Chloroform-d) δ 10.39 (s, 1H), 9.10 (d, J=7.8 Hz, 1H), 8.23 (s, 1H), 7.38 (s, 1H), 7.24-7.14 (m, 3H), 7.04 (d, J=3.5 Hz, 1H), 6.57 (d, J=3.5 Hz, 1H), 6.21 (s, 1H), 4.26-4.09 (m, 1H), 3.54 (dd, J=384.1), 14.3 Hz, 2H), 2.98 (d, J=4.7 Hz, 3H), 2.67-2.58 (m, 1H), 2.48-2.40 (m, 1H), 2.12-2.05 (m, 1H), 2.05-1.99 (m, 1H), 1.67 (t, J=12.1 Hz, 1H), 1.63-1.50 (m, 1H), 1.25 (s, 3H), 1.18 (s, 3H); $^{13}C$ NMR (101 MHz, Chloroform-d) δ 170.6, 150.0, 143.5, 143.4, 143.3, 134.2, 129.4, 128.2, 126.8, 126.3, 120.9, 105.2, 103.7, 102.8, 54.2, 52.9, 48.3, 47.4, 45.7, 34.2, 30.4, 26.6, 16.6; HRMS (ESI, m/z) calculated for $C_{23}H_{28}ClN_5O$ $[M+H]^+$ 426.2055 found 426.2059.

4-((1-(4-Chlorobenzyl)-2,2-dimethylpiperidin-4-yl)amino)-N-methyl-1H-pyrrolo[2,3-b]pyridine-5-carboxamide 25"c The title compound was synthesized according to General procedure J. Yield: 10.4%; $^1H$ NMR (400 MHz, Methanol-$d_4$) δ 8.36 (s, 1H), 7.63-7.50 (m, 4H), 7.40 (d, J=3.5 Hz, 1H), 6.96 (d, J=3.6 Hz, 1H), 4.68-4.58 (m, 1H), 4.40 (dd, J=318.5, 13.2 Hz, 2H), 3.76-3.58 (m, 1H), 3.59-3.50 (m, 1H), 3.43 (d, J=10.4 Hz, 1H), 2.88 (s, 3H), 2.42 (d, J=11.6 Hz, 1H), 2.09 (t, J=13.0 Hz, 1H), 1.89-1.78 (m, 1H), 1.75 (s, 3H), 1.73 (s, 3H); $^{13}C$ NMR (101 MHz, Methanol-$d_4$) δ 169.2, 139.7, 137.5, 135.8, 134.5, 134.4, 130.5, 129.6, 125.4, 106.5, 105.2, 104.2, 65.3, 54.4, 47.5, 47.4, 44.5, 31.2, 27.3, 26.7, 18.5; HRMS (ESI, m/z) calculated for $C_{23}H_{28}ClN_5O$ $[M+H]^+$ 426.2055 found 426.2058.

INDUSTRIAL APPLICABILITY

The compound of the present invention can exhibit therapeutic effects on a variety of diseases, for example, inflammatory diseases, autoimmune diseases, myeloproliferative diseases, and human cancers due to its ability to regulate signal transduction at the level of JAK kinases. Therefore, the present invention is applicable to a wide variety of fields, including medicine, nursing, pharmacology, pharmaceutics, hygienics, and public health.

The invention claimed is:

1. A compound represented by Formula II or a pharmaceutically acceptable salt thereof, Formula III or a pharmaceutically acceptable salt thereof, Formula IV or a pharmaceutically acceptable salt thereof, Formula VII or a pharmaceutically acceptable salt thereof, Formula VIII or a pharmaceutically acceptable salt thereof, or Formula IX or a pharmaceutically acceptable salt thereof:

[Formula II]

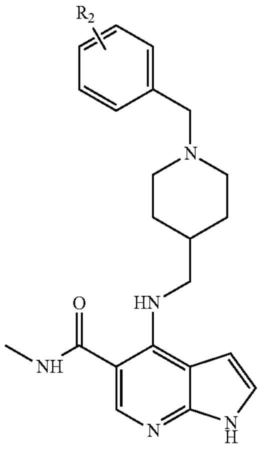

wherein $R_2$ is hydrogen, a halogen, a cyano group, or a $C_1$-$C_3$ alkoxy group,

[Formula III]

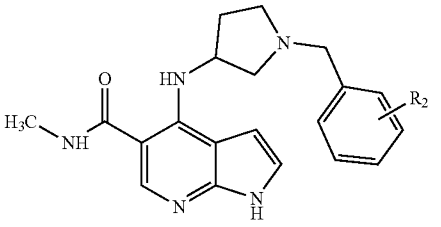

wherein $R_2$ is hydrogen, a halogen, a cyano group, or a $C_1$-$C_3$ alkoxy group,

[Formula IV]

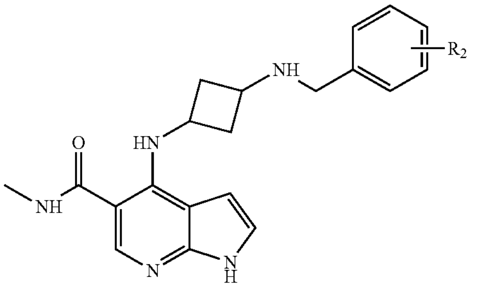

wherein $R_2$ is hydrogen, a halogen, a cyano group, or a $C_1$-$C_3$ alkoxy group,

[Formula VII]

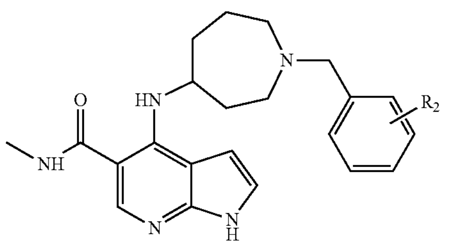

wherein $R_2$ is hydrogen, a halogen, a cyano group, or a $C_1$-$C_3$ alkoxy group,

[Formula VIII]

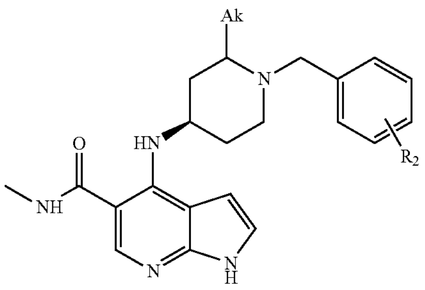

wherein Ak is a $C_1$-$C_3$ alkyl group, and $R_2$ is hydrogen, a halogen, a cyano group, or a $C_1$-$C_3$ alkoxy group, and

[Formula IX]

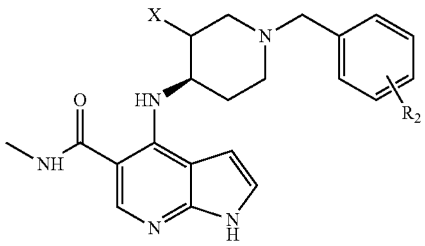

wherein X is a halogen and $R_2$ is hydrogen, a halogen, a cyano group, or a $C_1$-$C_3$ alkoxy group.

2. A pharmaceutical composition for treating or preventing an autoimmune disease or cancer comprising the compound or pharmaceutically acceptable salt thereof according to claim 1.

3. The pharmaceutical composition according to claim 2, wherein the autoimmune disease is atopic dermatitis, psoriasis, skin rash, contact dermatitis, multiple sclerosis, rheumatoid arthritis, psoriatic arthritis, juvenile arthritis, type I diabetes, lupus, inflammatory bowel disease, Crohn's disease, severe myasthenia gravis, immunoglobulin nephropathy, myocarditis or autoimmune thyroid disorders.

4. The pharmaceutical composition according to claim 2, wherein the cancer is pancreatic cancer, prostate cancer, lung cancer, head and neck cancer, breast cancer, colon cancer, ovarian cancer, gastric cancer, hepatic cancer, Castleman's disease, multiple myeloma, lymphoma, melanoma, neuroblastoma, glioblastoma, systemic mastocytosis or leukemia.

* * * * *